(12) United States Patent
Nicolas et al.

(10) Patent No.: US 7,273,758 B2
(45) Date of Patent: Sep. 25, 2007

(54) METHODS FOR INDUCING TARGETED STIMULATION OF MEIOTIC RECOMBINATION AND KITS FOR PERFORMING SAID METHODS

(75) Inventors: Alain Nicolas, Paris (FR); Ana Pecina-Lopez, Orsay (FR); Alberto Pascual, Orsay (FR); Kathleen Smith, Paris (FR); Christine Mezard, Paris (FR); Minoo Rassoulzadegan, Nice (FR)

(73) Assignees: Centre National de la Recherche Scientifique (FR); Institut National de la Sante et de la Recherche Medicale (FR); Institut National de la Recherche Agronomique and Institut Curie (FR)

( * ) Notice: Subject to any disclaimer, the term of this patent is extended or adjusted under 35 U.S.C. 154(b) by 446 days.

(21) Appl. No.: 10/199,762

(22) Filed: Jul. 19, 2002

(65) Prior Publication Data

US 2004/0033494 A1 Feb. 19, 2004

(51) Int. Cl.
C12N 15/87 (2006.01)
C12N 15/82 (2006.01)
C12N 15/80 (2006.01)
C12N 15/81 (2006.01)

(52) U.S. Cl. .................. 435/463; 435/468; 435/471

(58) Field of Classification Search ................ 435/463, 435/468, 471, 483, 437
See application file for complete search history.

(56) References Cited

OTHER PUBLICATIONS

Alani et al., Analysis of wild-type and rad50 mutants of yeast suggests an intimate relationship between meiotic chromosome synapsis and recombination, 61 Cell (1990) 419-36.
Baudat & Nicolas, Clustering of meiotic double-strand breaks on yeast chromosome III, 94 Proc. Natl. Acad. Sci. (1997) 5213-18.
Baudat et al., Chromosome synapsis defects and sexually dimorphic meitoci progression in mice lacking Spo11, 6 Molecular Cell (2000) 989-98.
Bergerat et al., An atypical topolsomerase II from archaea with implications for meiotic recombination, 386 Nature (1997) 414-17.
Beretta et al. Tethering a type IB topoisomerase to a DNA site by enzyme fusion to a heterologous site-selective DNA-binding protein domain, 59 Cancer Research (1999) 3689-97.
Borde et al. Use of a recombination reporter insert to define meiotic recombination domains on chromosome III of *Saccharomyces cerevisiae*, 19 Mol. & Cellular Biology (1999) 4832-42.
Diaz et al. Identification of Residues in Yeast Spo11p Critical for Meiotic DNA Double-Strand Break Formation 22 Mol. & Cellular Biology (2002) 1106-15.
Michael Esposito & Rochelle Esposito, The genetic control of sporulation in *Saccharomyces*, 61 Genetics (1969) 79-89.

Fromont-Racine et al., Toward a functional analysis of the yeast genome through exhaustive two-hybrid screens, 16 Nature Genetics (1997) 277-82.
Gerton et al., Global mapping of meiotic recombination hotspots and coldspots in the yeast *Saccharomyces cerevisiae*, 97 Proc. Natl. Acad. Sci. (2000) 11383-90.
Grelon et al. (2001). "AtSPO11-1 is necessary for efficient meiotic recombination in plants." Embo J 20(3): 589-600.
Kane & Roth (1974). Carbohydrate metabolism during ascospore development in yeast. J. Bacteriol. 118, 8-14.
Huibregtse et al. (1993). Gal4 protein binding is required but not sufficient for depression and induction of GAL2 expression. J.Biol. Chem. 268:22219-22222.
Keeney & Kleckner (1997). Meiosis-specific DNA double-strand breaks are catalyzed by Spo11, a member of a widely conserved protein family. Cell 88, 375-384.
Metzler-Guillemain, C. and B. de Massy (2000). "Identification and characterization of an SPO11 homolog in the mouse." Chromosoma 109(1-2): 133-8.
McKim, K. S. and A. Hayashi-Hagihara (1998). "mei-W68 in *Drosophila melanogaster* encodes a Spo11 homolog: evidence that the mechanism for initiating meiotic recombination is conserved." Genes Dev 12(18): 2932-42.
Ohta et al. (1994). Changes in chromatin structure at recombination initiation sites during yeast meiosis. EMBO J. 13, 5754-5763.
Petes, T.D. Meiotic recombination hot spots and cold spots, 2 Nature Rev. 360-369 (2001).
Ren et al. Genome-wide location and function of DNA binding proteins. Science 290, 2306-2309 (2000).
Rong, Y. S. and K. G. Golic (2000). "Gene targeting by homologous recombination in *Drosophila*." Science 288(5473): 2013-8.
Sage et al. (1999). "Temporal and spatial control of the Sycp1 gene transcription in the mouse meiosis: regulatory elements active in the male are not sufficient for expression in the female gonad." Mech Dev 80(1): 29-39.
Sikorski, R.S., and Hieter, P. (1989). A system of shuttle vectors and yeast host strains designed for efficient manipulation of DNA in *Saccharomyces cerevisiae*. Genetics 122, 19-27.
Smith et al. (2001). B-type cyclins CLB5 and CLB6 control the initiation of recombination and synaptonemal complex formation in yeast meiosis. Curr. Biol. 11, 88-97.
Vedel and Nicolas (1999). CYS3, a hotspot of meiotic recombination in *Saccharomyces cerevisiae*; effects of heterozygosity and mismatch repair functions on gene conversion and recombination intermediates. Genetics 151, 1245-1259.
Wach, A. (1996). PCR-synthesis of marker cassettes with long flanking homology regions for gene disruptions in *Saccharomyces cerevisiae*. Yeast 12, 259-265.

(Continued)

*Primary Examiner*—Nancy Vogel
(74) *Attorney, Agent, or Firm*—Lerner, David, Littenberg, Krumholz & Mentlik, LLP

(57) ABSTRACT

The invention pertains to methods, kits, molecules and cells to increase the rate or recombination and/or target recombination in dividing cells. In a particular aspect, the invention concerns methods and kits to induce targeted meiotic recombination.

9 Claims, 9 Drawing Sheets

OTHER PUBLICATIONS

Wu & Lichten (1994). Meiosis-induced double-strand break sites determined by yeast chromatin structure. Science 263, 515-518.

Wu & Lichten (1995). Factors that affect the location and frequency of meiosis-induced double-strand breaks in *Saccharomyces cerevisiae*. Genetics 140, 55-66.

Keeney, S. (2001). The mechanism and control of meiotic recombination initiation. Curr. Top. Dev. Biol. 52, 1-53.

Pirrotta, V. (1988). "Vectors for P-mediated transformation in *Drosophila*." Biotechnology 10: 437-56.

Ausubel, et al., Current Protocols in Molecular Biology (1988).

Sherman, et al., Methods in Yeast Genetics, Cold Spring Harbor, NY, Cold Spring Harbor Laboratory Press (1983).

GAL2/gal2-Bsp segregation

|  | 2+ 2- | 3+ 1- | 1+ 3- | Gene conversion |
|---|---|---|---|---|
| SPO11 | 213 | 2 | 3 | 2% |
| GAL4BD-SPO11 | 157 | 28 | 27 | 26% |

SEQUENCE LISTING

<160> NUMBER OF SEQ ID NOS: 11

<210> SEQ ID NO 1
<211> LENGTH: 29
<212> TYPE: DNA
<213> ORGANISM: ARTIFICIAL SEQUENCE
<220> FEATURE:
<223> OTHER INFORMATION: PRIMER
<220> FEATURE:
<221> NAME/KEY: MG133
<222> LOCATION: (1)..(29)
<223> OTHER INFORMATION:

<400> SEQUENCE: 1
gaaactcggg atccatggag ggaaaattc            29

<210> SEQ ID NO 2
<211> LENGTH: 26
<212> TYPE: DNA
<213> ORGANISM: ARTIFICIAL SEQUENCE
<220> FEATURE:
<223> OTHER INFORMATION: PRIMER
<220> FEATURE:
<221> NAME/KEY: MG134
<222> LOCATION: (1)..(26)
<223> OTHER INFORMATION:

<400> SEQUENCE: 2
ggagactcgc tcgaggctca aggaga              26

<210> SEQ ID NO 3
<211> LENGTH: 34
<212> TYPE: DNA
<213> ORGANISM: ARTIFICIAL SEQUENCE
<220> FEATURE:
<223> OTHER INFORMATION: PRIMER
<220> FEATURE:
<221> NAME/KEY: CM1
<222> LOCATION: (1)..(34)
<223> OTHER INFORMATION:

<400> SEQUENCE: 3
gactgcagaa agagatgaag ctactgtctt ctat       34

<210> SEQ ID NO 4
<211> LENGTH: 21
<212> TYPE: DNA
<213> ORGANISM: ARTIFICIAL SEQUENCE
<220> FEATURE:
<223> OTHER INFORMATION: PRIMER
<220> FEATURE:
<221> NAME/KEY: CM2
<222> LOCATION: (1)..(21)
<223> OTHER INFORMATION:

<400> SEQUENCE: 4
cggggcctcc atggccataa a                   21

<210> SEQ ID NO 5
<211> LENGTH: 15
<212> TYPE: DNA
<213> ORGANISM: ARTIFICIAL SEQUENCE
<220> FEATURE:
<223> OTHER INFORMATION: Pst 1 site and -8 to -1 bases upstream the
      AtSPO11-1 ATG and ATG

<400> SEQUENCE: 5

```
ctgcagaaag agatg                                                          15

<210> SEQ ID NO 6
<211> LENGTH: 32
<212> TYPE: DNA
<213> ORGANISM: ARTIFICIAL SEQUENCE
<220> FEATURE:
<223> OTHER INFORMATION: PRIMER
<220> FEATURE:
<221> NAME/KEY: CM3
<222> LOCATION: (1)..(32)
<223> OTHER INFORMATION:

<400> SEQUENCE: 6
ccatctcttt ctgcagtcaa aactgaaaaa tg                                       32

<210> SEQ ID NO 7
<211> LENGTH: 35
<212> TYPE: DNA
<213> ORGANISM: ARTIFICIAL SEQUENCE
<220> FEATURE:
<223> OTHER INFORMATION: PRIMER
<220> FEATURE:
<221> NAME/KEY: CM4
<222> LOCATION: (1)..(35)
<223> OTHER INFORMATION:

<400> SEQUENCE: 7
atgggcccgc ctttgtttta tctctcctca ccgta                                    35

<210> SEQ ID NO 8
<211> LENGTH: 11
<212> TYPE: DNA
<213> ORGANISM: ARTIFICIAL SEQUENCE
<220> FEATURE:
<223> OTHER INFORMATION: insert of 11 nucleotides just in 5' of the Pst
      1 cloning site in pVe CM5

<400> SEQUENCE: 8
cccatctctt t                                                              11

<210> SEQ ID NO 9
<211> LENGTH: 42
<212> TYPE: DNA
<213> ORGANISM: ARTIFICIAL SEQUENCE
<220> FEATURE:
<223> OTHER INFORMATION: PRIMER

<400> SEQUENCE: 9
gagattaatt aaggccatat gaagctactg tcttctatcg aa                            42

<210> SEQ ID NO 10
<211> LENGTH: 21
<212> TYPE: DNA
<213> ORGANISM: ARTIFICIAL SEQUENCE
<220> FEATURE:
<223> OTHER INFORMATION: PRIMER

<400> SEQUENCE: 10
aatcctgtta acaatgcttt t                                                   21

<210> SEQ ID NO 11
<211> LENGTH: 17
<212> TYPE: DNA
<213> ORGANISM: ARTIFICIAL SEQUENCE
<220> FEATURE:
<223> OTHER INFORMATION: consensus upstream activator sequence
      recognized by the DNA - binding domain of the Gal 4 protein
```

```
<220> FEATURE:
<221> NAME/KEY: misc_feature
<222> LOCATION: (4)..(14)
<223> OTHER INFORMATION: any nucleotide

<400> SEQUENCE: 11
cggnnnnnnn nnnncgg                                                17
```

METHODS FOR INDUCING TARGETED STIMULATION OF MEIOTIC RECOMBINATION AND KITS FOR PERFORMING SAID METHODS

FIELD OF THE INVENTION

In all eukaryotes, the rates of meiotic recombination between paternal and maternal chromosomes vary by several orders of magnitude at different chromosomal loci. In *Saccharomyces cerevisiae* and in other organisms, meiotic recombination is initiated by programmed DNA double-strand breaks (DSBs), a process that requires at least 15 proteins including Spo11, a widely conserved protein that likely catalyzes cleavage.

The present invention pertains to methods and kits to increase the rate of meiotic recombination in a cell and, more specifically, to induce targeted meiotic recombination. This invention is based on the fact that it is possible to target the initiation of meiotic recombination to a target site, by expressing in the cell a chimeric protein comprising a DNA binding domain operably linked to the Spo11 protein.

BACKGROUND AND PRIOR ART

In sexually reproducing organisms, the halving of the DNA content of a diploid germ line cell during the meiotic cell cycle allows the production of haploid gametes. During this process, recombination plays a dual role: it shuffles information along the lengths of homologous chromosomes, creating genetic diversity that is transmitted to progeny, and it ensures the proper segregation of homologs to opposite poles during the first of the two meiotic divisions. About a century ago, de Vries-predicted that exchanges take place between homologous maternal and paternal chromosomes during hereditary transmission. Soon thereafter in 1905, Bateson-discovered partial linkage between the petal color and pollen shape characters in Sweet Pea. These and successive discoveries in the emerging field of recombination led to the notion of genetic distances, as measured by the frequency of exchange (crossing-over) between linked markers, and to the development of linkage maps. In 1913, Sturtevant wrote "Of course, there is no knowing whether or not these distances as drawn represent the actual relative spacial distances apart of the factors". Since the advent of the molecular era, this prescient insight has been extensively verified by quantitative comparisons of genetic and physical distances. For all organisms, including the yeast *Saccharomyces cerevisiae*, *Arabidopsis thaliana*, *Drosophila melanogaster*, *Mus musculus*, and man, meiotic recombination rates (expressed as cM/kb) vary by several orders of magnitude along chromosomes. Recent studies of *S. cerevisiae* strongly suggest that most of this variation is related to the frequencies of initiating events (Baudat and Nicolas, 1997), but why it is relatively frequent at some loci (hotspots) and relatively infrequent at others (coldspots) remain unexplained.

In *S. cerevisiae*, meiotic recombination results from the formation and repair of programmed DNA double-strand breaks (DSBs) (for review, see for example: Smith and Nicolas, 1998). Numerous studies have shown that natural DSB sites are not evenly distributed and that cleavage frequencies vary 10-100-fold from site to site (Baudat and Nicolas, 1997; Gerton et al., 2000). The factors that determine whether a specific region or site is prone to DSB formation (and hence, recombination) are not completely understood, but they are known to act both locally and globally. Locally, gene organization and chromatin structure appear to be of paramount, and related, importance. Typically, most natural DSB sites are in promoter-containing regions (Baudat and Nicolas, 1997). At the HIS4 locus, two types of recombination hotspot have been distinguished, α (transcription factors-dependent but not transcription-dependent) and β (transcription factor independent) hotspots (reviewed by Petes, 2001). More notably, all known DSB sites are located in regions that are sensitive to DNase I or micrococcal nuclease (MNase I) in both mitotic and meiotic cells, suggesting that an open chromatin configuration is necessary for cleavage (Ohta et al., 1994; Wu and Lichten, 1994). However, local chromatin accessibility cannot be the sole arbiter of DSB site selectivity, because not all nuclease-hypersensitive sites are DSB sites.

Global determinants also control the distribution of DSBs. Both the fine mapping of DSB sites on yeast chromosome III and the genome-wide mapping of DSB sites have confirmed the existence of large subchromosomal domains hot or cold for DSB formation (Baudat and Nicolas, 1997; Gerton et al., 2000). The molecular basis of these DSB-proficient or -refractory domains has not been elucidated, but the finding that a recombination-proficient reporter inserted at various sites along chromosome III adopts local properties with respect to DNaseI sensitivity and frequencies of DSB formation and recombination demonstrates that domain-level controls are superimposed on local determinants (Borde et al., 1999). That is, a hot region can be made cold, but thus far the converse has not been observed: cold regions typically remain cold.

A consideration of the chromosomal variation in DSB frequencies must also take into account the influence of trans-acting factors. A large number of genes are required for DSB formation, including SPO11, MEI4, MER1, MER2/REC107, MRE2/NAM8, MRE11, RAD50, REC102, REC103/SKI8, REC104, REC114 and XRS2, but in most cases, their molecular roles are unknown. Null mutants for all of the above genes fail to carry out meiotic recombination and produce inviable spores. Three other meiosis-specific genes are required for full levels of DSBs: MEK1/MRE4 encodes a kinase that regulates the activities of the RED1 and HOP1 products, which are structural components of meiotic chromosomes. SPO11 encodes a protein that shares sequence similarity with the smaller subunit (Top6A) of the type II topoisomerase of the archaebacterium *Sulfobolus shibatae* (Bergerat et al., 1997). Spo11 remains covalently linked to the 5'-strand termini of DSB fragments in mutants (e.g. rad50S) that are defective for the 5' to 3' nucleolytic processing of DSB ends that normally precedes repair (Keeney et al., 1997), indicating that it is the catalytic component of the meiotic DSB cleavage activity. These and further molecular and genetic studies in fungi and higher eukaryotes have demonstrated that Spo11 orthologs are likely universally required for meiotic recombination, strongly suggesting that DSBs initiate meiotic recombination in most if not all eukaryotes. The use of site-directed mutagenesis to identify regions of Spo11 that contribute to strand cleavage and DNA binding has demonstrated the functional significance of structural motifs conserved throughout the Spo11/Top6A family (Bergerat et al., 1997; Diaz et al., 2002). Interestingly, variations in the level and distribution of DSBs at the his4::LEU2 hotspot in some spo11 mutants suggests that Spo11 is not only involved in the cleavage activity but also contributes to the choice of site for DSB formation, at least locally (Diaz et al., 2002).

SUMMARY OF THE INVENTION

The inventors have fused Spo11 to the DNA-binding domain of the Gal4 protein (Gal4BD), creating a Gal4BD-Spo11 fusion protein. The Gal4 protein is one of the best characterized transcriptional activators in *S. cerevisiae* and is required for the expression of genes involved in galactose catabolism. The protein binds to a consensus upstream activator sequence ($UAS_{GAL}$) through its N-terminal domain and stimulates transcription via its C-terminal activation domain. In vitro and in vivo "footprint" analyses have defined a consensus 17-base pair sequence at $UAS_{GAL}$ sites ($CGGN_{11}CCG$) as sufficient for Gal4 binding. The inventors have then demonstrated, as explained in the examples, that this fusion protein could stimulate recombination in formerly cold regions, which led to the present invention.

One object of the present invention is a method for increasing recombination between homologous chromosomes in a dividing cell, comprising the steps of expressing a DBD-Spo11 protein (wherein DBD is a DNA binding domain), in a dividing cell.

The invention also pertains to a method for performing a targeted recombination between two or more polymorphisms carried by a same chromosome in a cell, having said fusion protein expressed in a dividing cell and wherein the binding domain recognises a DNA sequence situated between or near said polymorphisms.

If necessary, a DNA sequence recognized by said DNA binding domain operably linked to Spo11 can be introduced into the cell genome, by standard techniques.

In the methods of the invention, the dividing cell might be a mitotic or a meiotic cell.

In these methods, the cell can comprise artificial chromosomes carrying one or more sequence(s) recognized by the DNA binding domain operably linked to the Spo11 protein.

If necessary, the nucleic acid encoding the DBD-Spo11 fusion protein is stably integrated into the cell genome.

Another aspect of the present invention is a method for inducing meiotic recombination in artificial chromosomes in a cell, comprising the introduction into a meiotic cell of a nucleic acid encoding a DBD-Spo11 fusion protein, wherein the DNA binding domain recognises at least one sequence of said artificial chromosome.

According to one implementation of this method, the cell is a yeast, the artificial chromosome is a YAC consisting of yeast or non-yeast DNA having one or more sites with a $CGGN_{11}CGG$ sequence (SEQ ID NO: 11), and the fusion protein is a Gal4BD-Spo11 fusion protein.

The invention also concerns a method for generating variants of an organism, comprising the steps of inducing a meiotic recombination using a DBD-Spo11 fusion protein expressed in a meiotic cell, and having the meiotic recombination occur at a higher rate and/or at different loci of the homologous chromosomes of the meiotic cells.

This method can further comprise a step of screening said variants for the presence of two or more characters.

In the same way, the present invention encompasses a method for analysing the genome of an organism, comprising the steps of generating variants of said organism, by performing the above method, performing a genetic analysis and a phenotypic analysis of certain characters of said variants, and analysing the genome of said organism.

All the methods according to the invention can be performed in any kind of eukaryotic cells and organisms, such as fungi, plants, and animals.

An other aspect of the present invention is a kit for performing the methods described above, containing a nucleic acid encoding a fusion protein comprising a DNA binding domain operably linked to a Spo11 protein, wherein said fusion protein is capable of inducing meiotic recombination in formerly cold regions. Such a kit can further comprise a nucleic acid carrying a target sequence recognized by said DNA binding domain operably linked to a Spo11 protein.

The nucleic acids of the kit according to the invention can be comprised in a vector, which can be any kind of vector, such as, for example, plasmids or any kind of replicative DNAs, complexed with transfecting agents if necessary, or phages, or virus.

The invention also pertains to a eukaryotic cell expressing a fusion protein comprising a DNA binding domain operably linked to a Spo11 protein, wherein said fusion protein is capable of inducing meiotic recombination in formerly cold regions of the genome of said eukaryotic cell.

This eukaryotic cell can be for example a fungus, a plant cell, a mammalian cell, or an insect cell.

Another aspect of the present invention concerns nucleic acids encoding a fusion protein comprising a DNA binding domain operably linked thereto, wherein said Spo11 protein is, for example, the AtSpo11 protein from *Arabidopsis thaliana* or the murine Spo11 protein.

(A) The plasmid pAP1 containing the GAL4BD-SPO11 fusion under the control of the ADH1 promoter (pADH1) and terminator (tADH1) was constructed as described in Experimental Procedures. The amino acid residues derived from the Gal4BD and Spo11 proteins are indicated above and below, respectively. (B) For Northern analysis, total RNA was prepared from SPO11 (ORD5740) and GAL4BD-SPO11 (ORD5806) cells during vegetative growth (Y) or at different times after transfer to sporulation medium and hybridized with a SPO11 probe. Blots were rehybridized with an ACT1 probe to provide a basis of comparison. (C) Quantification of the levels of SPO11 (circles) and GAL4BD-SPO11 (squares) transcript with respect to the level of ACT1 mRNA over the course of meiosis. (D) The Gal4BD-Spo11 protein was detected by Western blot analysis using an anti-Gal4(DBD) antibody. The same amount of protein being loaded on each lane, the fusion protein is present at the same level in ORD5806 cells throughout the meiotic cycle. No signal was detected for spo11Δ diploids (ORD5805) in meiosis.

FIG. 2. Meiotic DSB Formation at the Natural YCR043c-YCR048w, ARG4 and CYS3 hotspots in SPO11 and GAL4BD-SPO11 Diploids Genomic DNA was prepared from SPO11 (ORD1181) and GAL4BD-SPO11 (ORD5807) diploids taken at the indicated time after transfer to sporulation medium and DSBs were detected by Southern analysis. These strains are homozygous for the rad50S::URA3 allele, which permits DSB formation but prevents resection and repair (Alani et al., 1990). At the right of each gel a map of the region shows ORFs (open arrows indicate transcriptional sense), DSB sites (arrows), and the positions of the probes.

(A) DSB formation in the YCR043c-YCR048w region. DNA was digested with AseI and probed with a YCR048w internal fragment. Putative Gal4 consensus binding sequences in the YCR048w ORF are shown as black bars. (B) Quantification of prominent DSBs in the SPO11 and GAL4BD-SPO11 cells shown in FIG. 2A. The sums of the frequencies of DSB formation in the YCR046c promoter (1), the YCR047c-YCR048w promoter (2), and the YCR048w ORF (3) are represented as a histogram. These sums account for ≧99% of the total DSBs detected in the YCR043c-YCR048w region. (C) DSB formation at the ARG4 locus. DNA was digested with SnaBI and probed with an ARG4 internal fragment. The asterisk indicates a cross hybridizing band. (D) DSB formation at the CYS3 locus. DNA was digested with HindIII and probed with a FUN36 internal fragment.

FIG. 3. GAL4BD-SPO11-Promoted DSBs at Loci with $UAS_{GAL}$ Sequences

Genomic DNA was prepared from SPO11 (ORD1181) and GAL4BD-SPO11 (ORD5807) diploids and analysed as described in FIG. 2. $UAS_{GAL}$ sequences are indicated as boxes. (A) DSB formation at the GAL2 locus. DNA was digested with XbaI-NcoI and probed with a GAL2 internal fragment. (B) DSB formation at the GAL1,7,10 locus. DNA was digested with ClaI-AatII and probed with a GAL1 internal fragment.

Figure 4A:
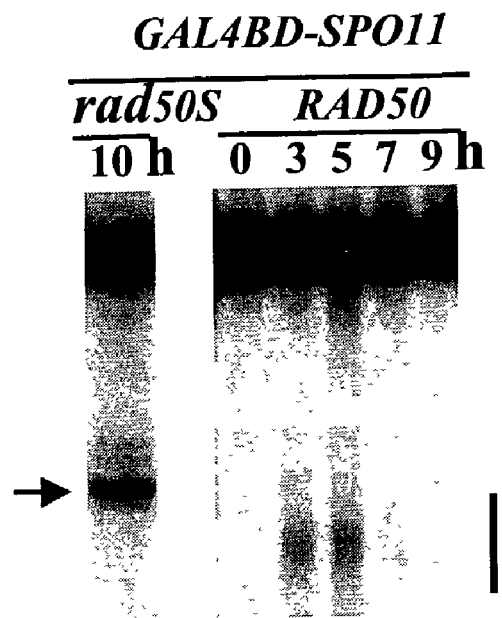
Figure 4B:
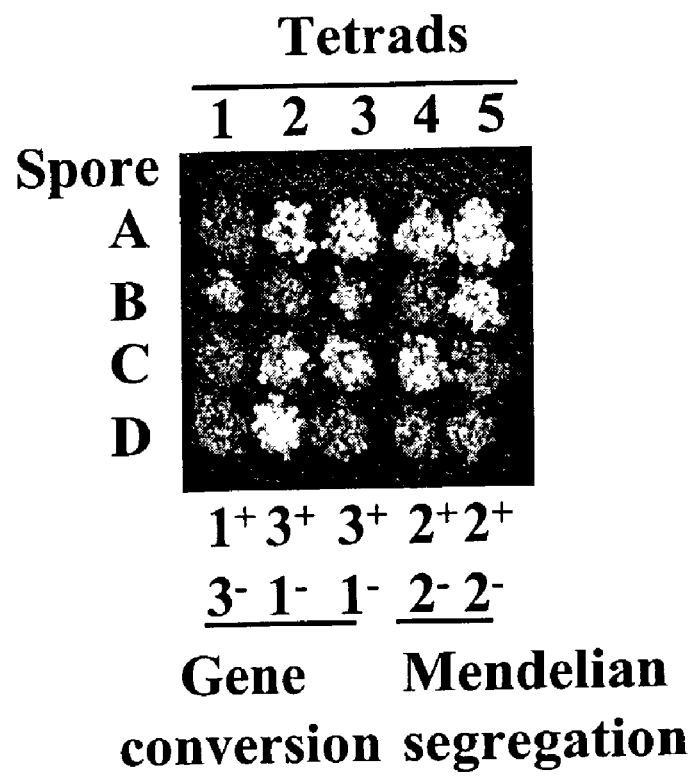

FIG. 4. Recombination is Stimulated at the GAL2 Locus in a GAL4BD-SPO11 Strain (A) DSB formation at the GAL2 locus in a RAD50 strain (ORD5806). Genomic DNA was digested with XbaI-NcoI and probed with a GAL2 internal fragment. Arrow at left shows DSBs at the GAL2 $UAS_{GAL}$ site in an isogenic rad50S strain (ORD 5807); the bar at right indicates the extent of the "smear" of DSB fragments. (B) Segregation of the GAL2 and gal2-Bsp alleles among progeny of a GAL4BD-SPO11 diploid (ORD6626). Tetrads were dissected on YPD and colonies were replica plated to YPGal. The gal2-Bsp allele confers a slow growth phenotype. Gene conversions (3+:1−and 1+:3−) and mendelian (2+:2−) segregation patterns can be seen in this example. (C) Meiotic gene conversion frequencies at the GAL2 locus in GAL4BD-SPO11 (ORD6626) and SPO11 (ORD6632) diploids heterozygous for the GAL2 and gal2-Bsp alleles.

Figures 4C, 5:
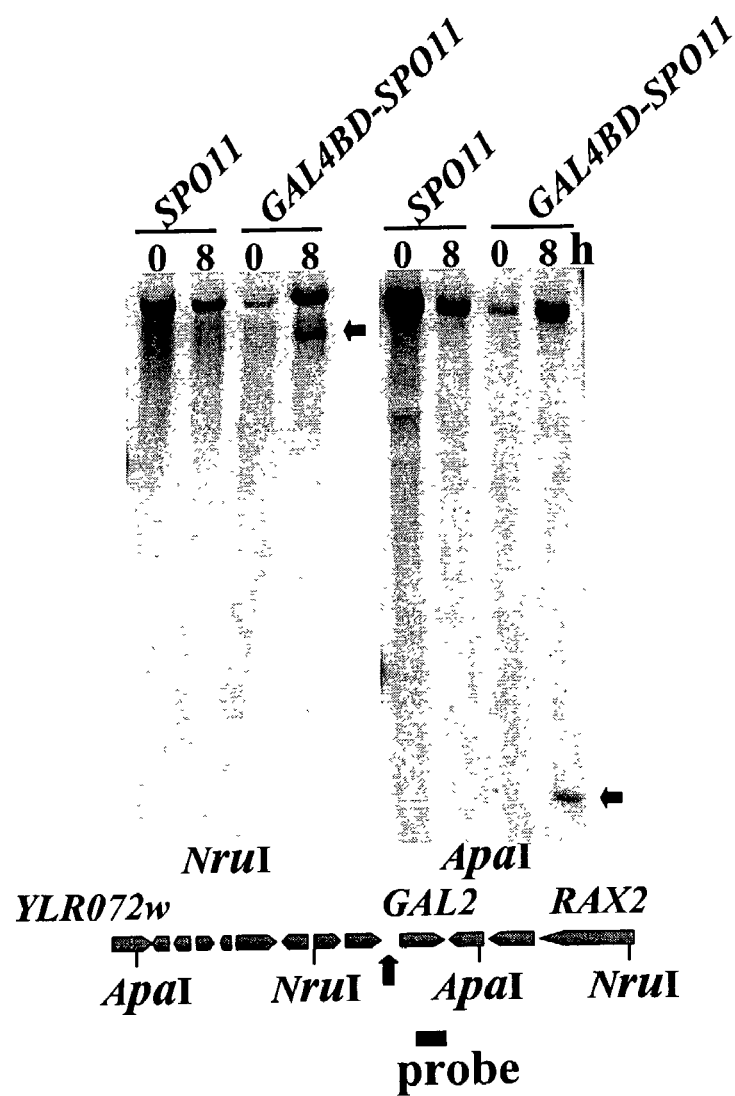

FIG. 5. The GAL2 Locus is Located in a Cold Region

Southern blot analysis of DSB formation in a 20 kb interval centered on the GAL2 locus. Meiotic DNA from SPO11 (ORD1181) and GAL4BD-SPO11 (ORD5807) diploids was digested with the indicated restriction enzymes and probed with a GAL2 internal fragment. The schematic shows the transcriptional senses of genes and relevant restriction sites. Arrows indicate DSB sites.

Figure 6:
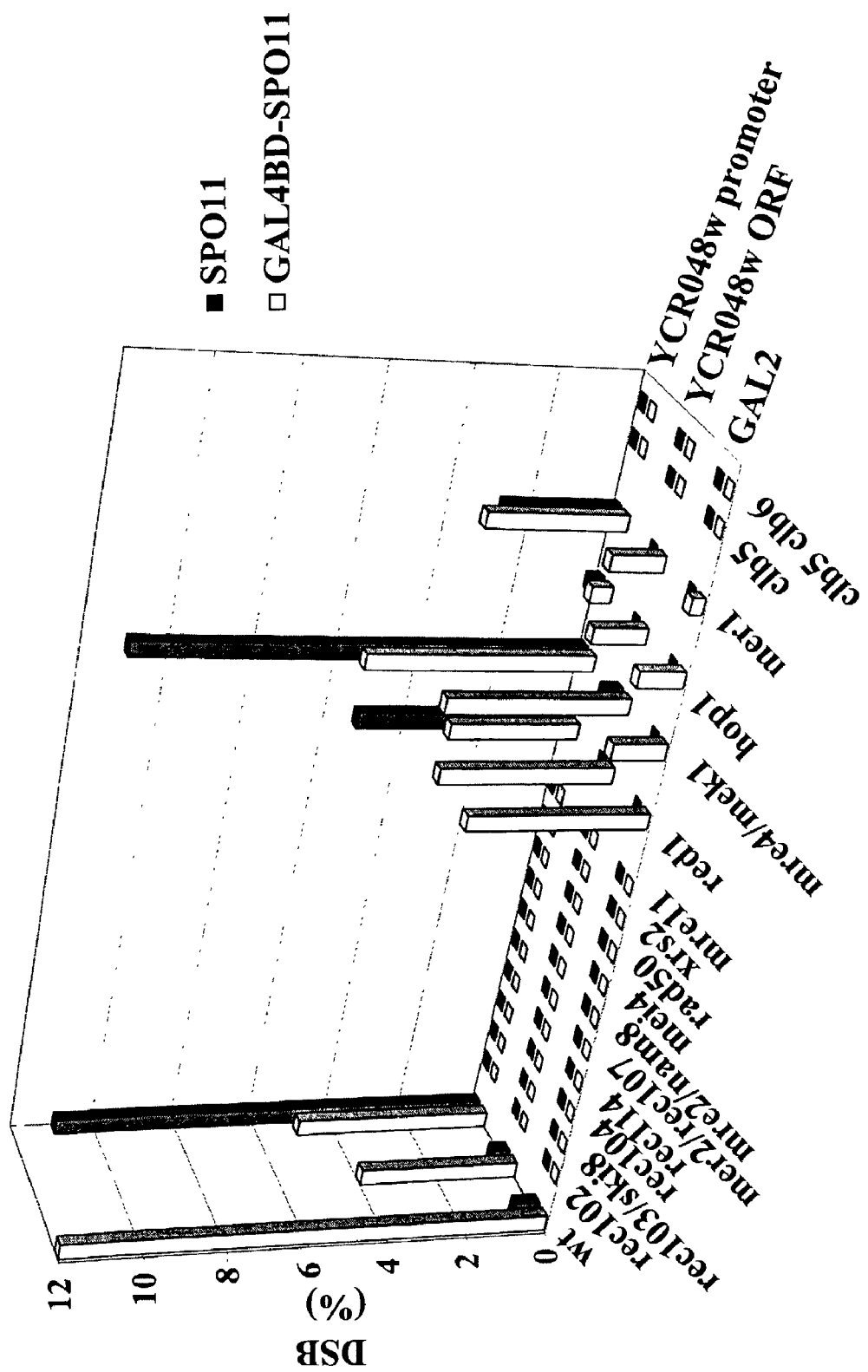

FIG. 6. Genetic Requirements for DSB Formation in SPO11 and GAL4BD-SPO11 Strains Southern blot analyses were carried out as in FIGS. 2 and 3 to measure meiotic DSB frequencies (z axis) at the GAL2 locus, YCR048w ORF and YCR048w promoter (y axis) in diploids carrying the SPO11 or GAL4BD-SPO11 constructs (black or white bars, respectively), in wild-type and mutant (as indicated on the x axis) backgrounds. The genotypes of all strains assayed are listed in Table I. DSB frequencies were determined at 8 or 10 hr after transfer to sporulation medium.

DETAILED DESCRIPTION OF THE PREFERRED EMBODIMENTS

Throughout this application, several words are employed, the meaning of which should be understood according to the following definitions:

A fusion protein is a chimeric protein comprising at least two moieties originating from different sources. It is usually the product of a fusion gene comprising coding sequences originating from different sources, wherein said coding sequences are in frame.

The present invention involves fusion proteins comprising a DNA binding domain operably linked to a Spo11 protein. In these fusions, the DNA binding domain, or DBD, is any domain of any protein, which has the property to bind to DNA, whether this binding is sequence-specific or not. Examples of non-specific DBDs are the topisomerases like TopoI and TopoII and strand-exchange proteins such as Rad 51, and examples of sequence-specific DBDs are the Gal4 DBD (thereafter noted Gal4BD) or lexA repressor. Of course, these examples are purely indicative, and other DBDs can be used to perform the invention.

The second moiety of the fusion proteins according to the invention is a Spo11 protein. This term designates the protein product of the SPO11 gene identified in S. cerevisiae (Esposito and Esposito, 1969), but also the ortholog proteins of Spo11, i.e., the products of ortholog genes of the SPO11 gene, being understood that ortholog genes are homologous genes that are found in two different taxa and are performing the same function in each taxon. Other examples of Spo11 proteins are the AtSpo11 of Arabidipsis thaliana (Grelon et al, 2001), and the murine mSpo11, the sequence of which is described in (Baudat and Keeney, 2000).

The two moieties of the fusion proteins involved in the present invention—the DBD and Spo11—are "operably linked", which means that the fusion protein retains the ability of binding to the DNA through the DBD moiety (in a sequence-specific manner if the DBD is sequence-specific), and retains also the initial functions of Spo11 (generating double strand breaks). Depending of the DBD and the Spo11, the DBD moiety can be located at the N-terminal or at the C-terminal extremity of the fusion. Alternatively, two DBDs (possibly different ones) can be fused to Spo11, one at each extremity of the protein.

Other definitions will appear in the following detailed description of preferred embodiments.

Interestingly, as described in the Examples, the present invention provides a novel way of substantially increase the frequency of homologous recombination during meiosis and to target this recombination by a simple modification of the Spo11 protein. Previous reports have described the use of site-specific nucleases such as I-ScelI, HO or VDE to locally stimulate meiotic homologous recombination. The present method of adding a heterologous DNA binding domain to Spo11 provides an alternative strategy with distinct features and practical advantages. For example, this approach exploits naturally occurring chromosomal sites of low complexity, thereby multiplying the number of potential targets without requiring the prior introduction of a specific sequence nor the deletion of the resident SPO11 gene. Also, cleavage remains under normal physiological control with respect to cis and trans acting determinants, and as a consequence, DSBs are repaired by the homologous recombination pathway, allowing for the production of viable gametes and recovery of novel recombinants.

The present invention pertains to a method for increasing recombination between homologous chromosomes in a dividing cell, comprising the steps of:
 (i) introducing into said cell, a nucleic acid encoding a fusion protein comprising a DNA binding domain operably linked to a Spo11 protein, and
 (ii) having the cell divide, so that the recombination between homologous chromosomes in said cell is increased.

Indeed, as described below in Example 1, the inventors have evidenced that a Gal4BD-Spo11 protein could induce double stranded breaks in natural hotspots and, in addition, at the level of Gal4BD consensus sequences, even if they are located in cold regions of the genome. If necessary, the above method can further comprise, before step (ii), a step of introducing into said cell's genome, a DNA sequence recognized by said DNA binding domain operably linked to a Spo11 protein. The introduction of a number of such sequences will increase the rate of homologous recombination in the cell. Moreover, these sequences can be introduced at certain locations, thereby enabling a targeting of recombination, as described in more details below.

This method can be performed within a cell that comprises artificial chromosomes carrying one or more sequence(s) recognized by said DNA binding domain operably linked to the Spo11 protein. Indeed, as explained in Example 5, artificial chromosomes do not always recombine during meiosis, which leads to problems of segregation, and therefore to the loss of these chromosomes in some daughter cells.

In the method described above, the nucleic acid introduced into the cell in step (i), encoding the DBD-Spo11 fusion protein, can be stably integrated into the cell genome. Alternatively, this nucleic acid can remain episomal, whether in a transient or in a stable episome. A transient episome is a DNA molecule which remains outside the cell genome and will not always be transmitted to the daughter cells during cell divisions. It can be, for example, and depending on the host cells, a plasmid or an adenoviral vector genome. A stable episome is one which will be replicated and transmitted to daughter cells, such as, for example, a replicon carrying the oriP-EBNA-1 system from Epstein-Barr virus. Importantly, the inventors have demonstrated that targeted meiotic double-strand breaks can be induced by Gal4BD-Spo11 encoded by a plasmid introduced into the cell, without altering the resident SPO11 gene.

In a specific embodiment of the above method, which is illustrated in Example 1, the cell is a yeast and the nucleic acid introduced into it in step (i) encodes a Gal4BD-Spo11 fusion protein.

The present invention also concerns a method for performing a targeted recombination between two or more polymorphisms carried by a same chromosome in a cell, comprising the steps of:
 (i) introducing into said cell, a nucleic acid encoding a fusion protein comprising a DNA binding domain operably linked to a Spo11 protein, wherein said DNA binding domain recognizes a sequence situated between said two or more polymorphisms, and
 (ii) having the cell divide, so that the recombination between said two or more polymorphisms in said cell occurs.

A method for targeting a gene conversion in a cell, i.e., a local transfer of one or several polymorphism(s), resulting in unidirectional acquisition of said polymorphism by a chromosome, is also part of the invention. Indeed, the present invention enables the obtention of different haplotypes by gene conversion as well as by crossing-over. This later method comprises the following steps:
 (i) introducing into the cell, a nucleic acid encoding a fusion protein comprising a DNA binding domain operably linked to a Spo11 protein, wherein said DNA binding domain recognises a sequence situated near the polymorphism(s) to be transferred, and
 (ii) having the cell divide, so that the gene conversion occurs.

These methods can be particularly useful to study interactions between genes which usually segregate together, in particular genes that are located in a DNA region which does not comprise any hotspot. If necessary, these methods can further comprise before step (ii), a step of introducing into said cell's genome, between or near said polymorphism(s), a DNA sequence recognized by the DNA binding domain operably linked to a Spo11 protein.

In the method for performing a targeted recombination according to the invention, the cell can comprise artificial chromosomes carrying one or more sequence(s) recognized by the DBD operably linked to the Spo11 protein. Hence, this method helps targeting homologous recombination at specific locations along the artificial chromosomes.

In a preferred embodiment of the above methods, the cell is a yeast, and the Spo11 moiety comes from *S. cerevisiae*. Optionally, the DBD is the Gal4BD.

In a preferred embodiment of the methods of the invention, the cell division performed in step (ii) is a meiosis. Some cells, such as yeast, can initiate a meiosis and then return to a mitosis, by a process called "return to growth", or RTG. In such cells, the method can be performed by inducing recombination at an early step of meiosis, and then have the cells return to growth.

Another aspect of the present invention is a method for inducing meiotic recombination in artificial chromosomes in a cell, comprising the steps of:
 (i) introducing into said cell, a nucleic acid encoding a fusion protein comprising a DNA binding domain operably linked to a Spo11 protein, wherein said DNA binding domain recognizes one or more sequence(s) carried by said artificial chromosome, and
 (ii) having the cell divide, so that the meiotic recombination occurs between artificial chromosomes.

As mentioned above, artificial chromosomes do not necessarily recombine during meosis, thereby incurring segregation troubles. This is a major drawback limiting the use of artificial chromosomes. In this specification, the term "artificial chromosome" not only designates fully artificial chromosomes (such as YACs), but also homeologous and heterologous chromosomes from other strains. For example in yeast, it is possible to obtain hybrid strains comprising chromosomes originating from different wild type strains. Such chromosomes, when they have a relatively high percentage of identity, are said "homeologous", whereas chromosomes being less close in sequence are "heterologous". In hybrid yeast, heterologous and, to a less extent, homeologous chromosomes fail to recombine during meosis.

By enabling meiotic recombination between artificial chromosomes in a cell, the present invention opens new interesting prospects, in particular in industries involving yeast. For example, in the brewery field, yeast are often hybrid strains, since the skilled artisan tries to combine in the same strain several advantageous characters from different wild-type strains. The selection of optimal strains is not easy, especially because these strains are unable to sporulate, for the reason mentioned above.

The method of the invention generally helps recombine haplotypes in a cell. The recombinations obtained by this method can be allelic, when they occur between the same positions on homologous chromosomes, or ectopic, when they happen between regions that are only locally homologous. Hence, the method enables to create translocations between the chromosomes. Consequently, the method according to the invention, by enabling recombination between the different chromosomes in cells during cell division, could no doubt increase the performance of the yeast strains mentioned above and, more generally, of any kind of strains used in the industry. Interestingly, as mentioned above, it is possible to induce the recombination at an early step of meiosis, and then let the cell come back to mitosis, by the RTG process.

In a specific embodiment of the method for inducing recombination in artificial chromosomes, wherein the cell is a yeast, the artificial chromosome is a YAC having one or more sites with a $CGGN_{11}CGG$ sequence, and the fusion protein is a Gal4BD-Spo11 fusion protein.

The recombination of artificial chromosomes can also lead to a wider use of this tool in protein synthesis in cultures of eukaryotic cells, for example in the pharmaceutical field.

The present invention also concerns a method for generating variants of an organism, comprising the steps of:
 (i) introducing into a cell of said organism, a nucleic acid encoding a fusion protein comprising a DNA binding domain operably linked to a Spo11 protein, wherein said DNA binding domain recognizes one or more sequence(s) carried by said cell's genome;
 (ii) having said cell perform a meiosis, so that meiotic recombination occurs between homologous chromosomes of said cell, at a higher rate and/or at different loci than in a natural meiosis of said organism; and
 (iii) generating variants of said organism with the cell obtained in step (ii).

In this method, the term "variant" should be understood broadly, and designates an organism which presents at least one phenotypic or genotypic difference having regard to its parent(s). Variants resulting from recombination between homologous chromosomes will result from reassociation of genetic polymorphisms, defined by the DNA sequence, occurring between or within genes. More generally, a variant here designates an organism, the haplotype of which is different from the haplotype(s) of its parent(s).

As previously described, Spo11 is homologous to an archebacterial topoisomerase (Bergerat, de Massy, 1997). However, the methods according to the present invention are preferably performed in eukaryotic cells. These cells can be for example selected from the group consisting of a fungus, a plant cell, a mammalian cell, and an insect cell. The experimental part described below illustrates examples of such cells, with *S. cerevisiae* for the fungi, *A thaliana* for the plants, mouse for the mammalians, and *Drosophila* for the insects. All the same, in the above method for generating variants of an organism, this organism can be selected from the group consisting of a fungus, a plant, a non human mammal, and an insect.

The method for generating variants of an organism, according to the invention, can further comprise a step of screening the obtained variants for the presence of two or more characters. This method, by increasing the recombination rate and/or by inducing targeted meiotic recombination, enables the rapid obtaining of variants combining different characters from the parent cells. Hence, it can decrease drastically the amount of individuals that must be screened to find one presenting a certain combination of alleles.

The above-described method leads to another aspect of the present invention, which is a method for analysing the genome of an organism, comprising the steps of:
 (i) generating variants of said organism, according to the method of the invention;
 (ii) performing a genetic analysis and a phenotypic analysis of certain characters of said variants; and
 (iii) analysing the genome of said organism.

Indeed, the rapid obtaining of a larger number of variants undoubtedly facilitates establishing correlation between genotypes and phenotypes, since the amount of organisms (for example, mice) that must be screened to find some with the desired allele(s) is reduced.

The variants obtainable by the method of the invention can be used in experimental models for screening the effect of a compound of any kind, for example in the course of the development of drugs, or for obtaining an appropriate host cell suitable for a recombinant gene expression.

The present invention also pertains to a kit for performing the methods described above, containing a nucleic acid encoding a fusion protein comprising a DNA binding domain operably linked to a Spo11 protein, wherein said fusion protein is capable of inducing double strand breaks in formerly cold regions.

In this kit, Spo11 can have the sequence of a Spo11 protein from a cell selected from the group of a fungus, a plant cell, a mammalian cell, and an insect cell. Examples of such sequences are spo11 from *S. cerevisiae* (yeast), Atspo11 from *A. thaliana* (plant), the murine spo11 (mammal), and spo11 from *Drosophila* (insect). Of course, these examples are not restrictive, and any spo11 ortholog gene from any other organism can be used.

The kit of the invention can further comprise a nucleic acid carrying a target sequence recognized by said DNA binding domain operably linked to a Spo11 protein. This target sequence can be comprise in any kind of vector, for example in a cloning vector comprising a high number of restriction sites, so that constructs to insert this target sequence in the desired locus of the desired chromosome is facilitated.

The nucleic acid comprising the DBD-spo11 sequence can also be comprised in a vector. As mentioned above, the methods of the invention can be performed without integrating the DBD-spo11 gene into the cell genome. Therefore, and depending on the type of cells, a large variety of vectors are appropriate, such as plasmids, replicative DNAs, nuclic acids complexed with any kind of transfecting agents, phages, and viruses. Different viruses can be used as vectors to introduce the nucleic acid comprising the DBD-spo11 sequence into mammalian cells, some of which will integrate into the cell genome (such as retroviruses for example), whereas some will not (ex.: adenoviruses).

Also part of the present invention is an eukaryotic cell expressing a fusion protein comprising a DNA binding domain operably linked to a Spo11 protein, wherein said fusion protein is capable of inducing double strand breaks in formerly cold regions of the genome of said eukaryotic cell. Of course, the phrase "cold region", in this context, designates cold regions for meiotic recombination. In this cell, the DBD-spo11 gene is under the control of a promoter, which can be meiosis-specific or not. The cell according to the invention can also be engineered so that the expression of meiosis-specific proteins is modified, as explained in Example 6. This cell can be for example a fungus, a plant cell, a mammalian cell, or an insect cell.

Yet another aspect of the present invention concerns nucleic acids encoding a fusion protein comprising a DNA binding domain operably linked thereto, wherein said Spo11 protein is, for example, the AtSpo11 protein from *Arabidopsis thaliana* or the murine Spo11 protein.

EXAMPLES

The following examples can be performed using the experimental procedures described below:

Experimental Procedures

Plasmid Construction

To create the integrative plasmid pAP1, which encodes the Gal4BD-Spo11 fusion, the SPO11 ORF was generated by PCR and introduced as a BamHI/Pst1 fragment downstream of the sequence encoding the Gal4 DNA binding domain (Gal4BD) in the two-hybrid vector pAS2ΔΔ (Fromont-Racine, Rain et al. 1997). The in-frame N-terminal fusion of Gal4BD to Spo11 and the complete ORF were verified by sequencing. The kanMX4 drug resistance cassette (Wach, 1996) was inserted into a unique NruI site, and the 2μ replication origin was removed by replacing a BpmI-Bsu36I fragment with the corresponding fragment from pRS304 (Sikorski and Hieter, 1989) producing pAP1. To create pICM99, the GAL2 locus was amplified from genomic DNA and a subclone containing the promoter region and the first 655 bp of the GAL2 ORF was mutagenized with the QuikChange site-directed mutagenesis kit (Stratagene). This frameshift mutation generates a BspHI restriction site and gives rise to a truncated protein of 66 amino acids. The relevant fragment was sequenced to confirm the mutation and finally subcloned into pRS306 (Sikorski and Hieter, 1989), producing pICM99.

Yeast Strains

All yeast strains are isogenic derivatives of SK1 (Kane and Roth, 1974). They were obtained by transformation or crossing and their relevant genotypes are shown in Table I. XbaI-digested pAP1 was integrated at the trp1 locus by transformation using the lithium acetate/polyethylene glycol method (Ausubel et al., 1988). G418 (200 μg/ml) resistant transformants were selected and checked for tryptophan prototrophy. Correct targeting was verified by Southern analysis. The gal2-BspHI mutation was introduced at the GAL2 locus by the two-step replacement procedure using URA3 as a selectable marker (Ausubel et al., 1988). For transformation, pICM99 was linearized at the unique BglII site in the GAL2 ORF, and targeting was verified by PCR and Southern analysis. Retention of the desired point mutation among 5-fluoroorotate-resistant pop-out clones was confirmed by BspHI restriction analysis of amplified GAL2 fragments.

Media and Genetic Techniques

Standard media (YPD) and SD (0.67% yeast nitrogen base without amino acids, 2% glucose), supplemented when necessary with appropriate nutrients (Sherman et al., 1983), were used for vegetative growth. Meiotic cultures were prepared as described (Alani et al., 1990). Complete galactose medium YPGal, in which glucose was replaced by galactose (20 g/l), allowed segregation of the gal2-BspHI allele to be monitored. Spore viabilities were determined by dissecting four-spored asci produced in sporulation medium after 48 h.

Molecular Techniques

For detection and quantification of DSBs, genomic DNA was prepared from sporulating cells and subjected to Southern analysis. Parental and DSB bands were visualized with a Phosphorimager and quantified with the use of ImageQuant software (Molecular Dynamics) as described (Vedel and Nicolas, 1999). Northern analysis was performed as described (Smith et al., 2001). Whole cell extracts were prepared and analyzed by western blotting with an anti-Gal4 (DBD) antibody (Santa Cruz Biotechnology) using standard procedures (Ausubel et al., 1988).

Example 1

Targeted Stimulation of Meiotic Recombination in *Saccharomyces cerevisiae*

1.1. The Gal4BD-Spo11 Fusion Protein is Expressed in Meiosis

Figure 1A:
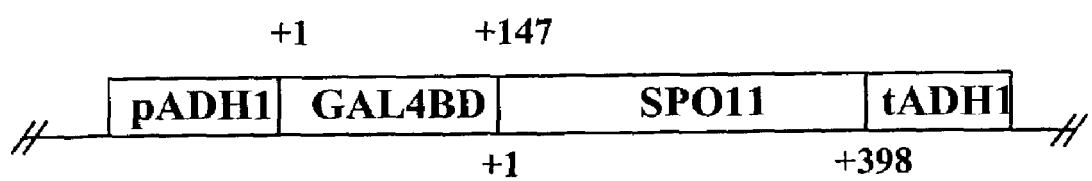
FIG. 1. Structure and Expression of GAL4BD-SPO11

A fusion encoding the DNA-binding domain of Gal4 (Gal4BD, amino acids 1-147) with the N-terminus of the full length *S. cerevisiae* Spo11 protein was placed under the control of the constitutive ADH1 promoter (FIG. 1A) and integrated at the TRP1 locus in a spo11Δ strain. Homozygous diploids were derived by genetic crosses (Table I).

TABLE I

Strain genotypes

| STRAIN | RELEVANT GENOTYPE |
| --- | --- |
| ORD1181 | a/α rad50S::URA3/" |
| ORD5740 | a/α arg4-nsp/arg4-bg LEU2/leu2 |
| ORD5805 | a/α spo11Δ::URA3/" arg4-bg/arg4-rV NUC1/nuc1Δ::LEU2 leu2/" |
| ORD5806 | a/α trp1::GAL4BD-SPO11-TRP1-KanMX/" spo11Δ::URA3/" arg4-bg/arg4-rV nuc1Δ::LEU2/" leu2/" |
| ORD5807 | a/α trp1::G4BD-SPO11-TRP1-KanMX/" spo11Δ::URA3/" rad50S::URA3/" arg4-bg/" NUC1/nuc1Δ::LEU2 leu2/" |
| ORD5817 | a/α trp1::GAL4BD-SPO11-TRP1-KanMX/" arg4-bg/ARG4 leu2/" |
| ORD5821 | a/α rec102Δ::URA3/" rad50S::LEU2/" leu2/" |
| ORD5828 | a/α trp1::GAL4BD-SPO11-TRP1-KanMX/" spo11Δ::URA3/" mre4::URA3/" rad50S::LEU2/" arg4-bg/arg4-rV leu2/" |
| ORD5845 | a/α mre4::URA3/" rad50S::LEU2/" arg4-bg/ARG4 leu2/" |
| ORD5846 | a/α mre2::URA3/" rad50S::LEU2/" leu2/" |
| ORD5849 | a/α trp1::GAL4BD-SPO11-TRP1-KanMX/" spo11Δ::URA3/" mre2::URA3/" rad50S::LEU2/" arg4-rV/" leu2/" |
| ORD5851 | a/α trp1::GAL4BD-SPO11-TRP1-KanMX/" spo11Δ::URA3/" rec104Δ::LEU2/" rad50S::URA3/" arg4-bg/" leu2/" |
| ORD5857 | a/α rec104Δ::LEU2/" rad50S::URA3/" leu2/" |
| ORD5859 | a/α trp1::GAL4BD-SPO11-TRP1-KanMX/" spo11Δ::URA3/" rec102Δ::URA3/" rad50S:LEU2/" arg4-rV/ARG4 leu2/" |
| ORD5879 | a/α trp1::GAL4BD-SPO11-TRP1-KanMX/" spo11Δ::URA3/" rec103::KanMX/"rad50S:: URA3/" arg4-bg/ARG4 leu2/" |
| ORD6534 | a/α trp1::GAL4BD-SPO11-TRP1-KanMX/" spo1Δ::URA3/" clb5::URA3/" clb6::TRP1/" rad50S::LEU2/" arg4-bg/" leu2/" |
| ORD6551 | a/α trp1::GAL4BD-SPO11-TRP1-KanMX/" spo11Δ::URA3/" clb5::URA3/" rad50S::LEU2/" arg4-bg/" leu2/" |
| ORD6591 | a/α mei4::URA3/" rad50S::LEU2/" arg4-bg/ARG4 leu2/" |
| ORD6593 | a/α rec103::KanMX/" rad50S::LEU2/" arg4-bg/ARG4 leu2/" |
| ORD6595 | a/α red1::URA3/" rad50S::LEU2/" arg4-bg/ARG4 leu2/" |
| ORD6598 | a/α rec114::KanMX/" rad50S::LEU2/" arg4-bg/"leu2/" |
| ORD6626 | a/α trp1::GAL4BD-SPO11-TRP1-KanMX/" spo11Δ::URA3/" arg4-bg/ARG4 GAL2/gal2-Bsp NUC1/nuc1Δ::LEU2 leu2/" |
| ORD6632 | a/α GAL2/gal2-Bsp LEU2/leu2 |
| ORD7414 | a/α mer1::LEU2/" rad50S::URA3/" arg4-rV/" leu2/" |
| ORD7419 | a/α hop1::LEU2/" rad50S::URA3/" arg4-rV/" leu2/" |
| ORD7420 | a/α trp1::GAL4BD-SPO11-TRP1-KanMX/" spo11Δ::URA3/" mei4::URA3/" rad50S::LEU2/" arg4-bg/ARG4 leu2/" |
| ORD7421 | a/α trp1::GAL4BD-SPO11-TRP1-KanMX/" spo11Δ::URA3/" rec114::KanMX/" rad50S::LEU2/" arg4-bg/ARG4 leu2/" |
| ORD7430 | a/α mre11Δ::KanMX/" rad50S::URA3/" arg-rV/ARG4 leu2/" |

TABLE I-continued

Strain genotypes

| STRAIN | RELEVANT GENOTYPE |
|---|---|
| ORD7443 | a/α trp1::GAL4BD-SPO11-TRP1-KanMX/" spo11Δ::URA3/" mer1::LEU2/" rad50S::URA3/" arg4-rVARG4 leu2/" |
| ORD7447 | a/α trp1::GAL4BD-SPO11-TRP1-KanMX/" spo11Δ::URA3/" red1::URA3/" rad50S::LEU2/" arg4-bg/" leu2/" |
| ORD7448 | a/α mer2::URA3/" rad50S::LEU2/"arg4-bg/ARG4 leu2/" |
| ORD7452 | a/α trp1::GAL4BD-SPO11-TRP1-KanMX/" spo11Δ::URA3/" rad50Δ::hisG/" com1::KanMX/" arg4-ndp/ARG4 leu2/" |
| ORD7454 | a/α trp1::GAL4BD-SPO11-TRP1-KanMX/" spo11Δ::URA3/" hop1::LEU2/" rad50S::URA3/" arg4-rV/ARG4 leu2/" |
| ORD7456 | a/α rad50Δ::hisG/" com1::KanMX/"arg4-nsp, bg/ARG4 LEU2/leu2 |
| ORD7459 | a/α trp1::GAL4BD-SPO11-TRP1-KanMX/" spo11Δ::URA3/" mer2::URA3/" rad50S::LEU2/" arg4-bg/ARG4 leu2/" |
| ORD7461 | a/α trp1::GAL4BD-SPO11-TRP1-KanMX/" spo11Δ::URA3/" mre11Δ::KanMX/" rad50S::LEU2/" arg4-bg/" leu2/" |
| ORD7466 | a/α xrs2Δ::LEU2/" com1::KanMX/" arg4-nsp,bg/ARG4 leu2/" |
| ORD7468 | a/α trp1::GAL4BD-SPO11-TRP1-KanMX/" spo11Δ::URA3/" xrs2Δ::LEU2/" com1::KanMX/" arg4-nsp,bg/ARG4 leu2/" | strains are ho::LYS2/" lys2/" ura3/" trp1/". All strains were constructed for this work except ORD1181 (Baudat and Nicolas, 1997) and ORD5740 (Smith et al, 2001).

Figure 1B:
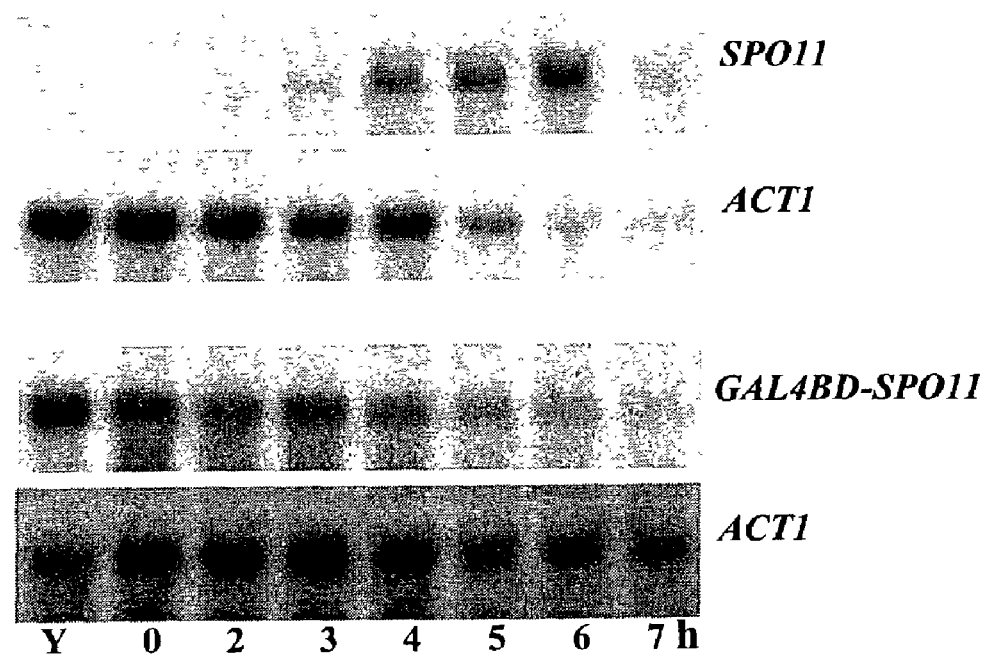
Figure 1C:
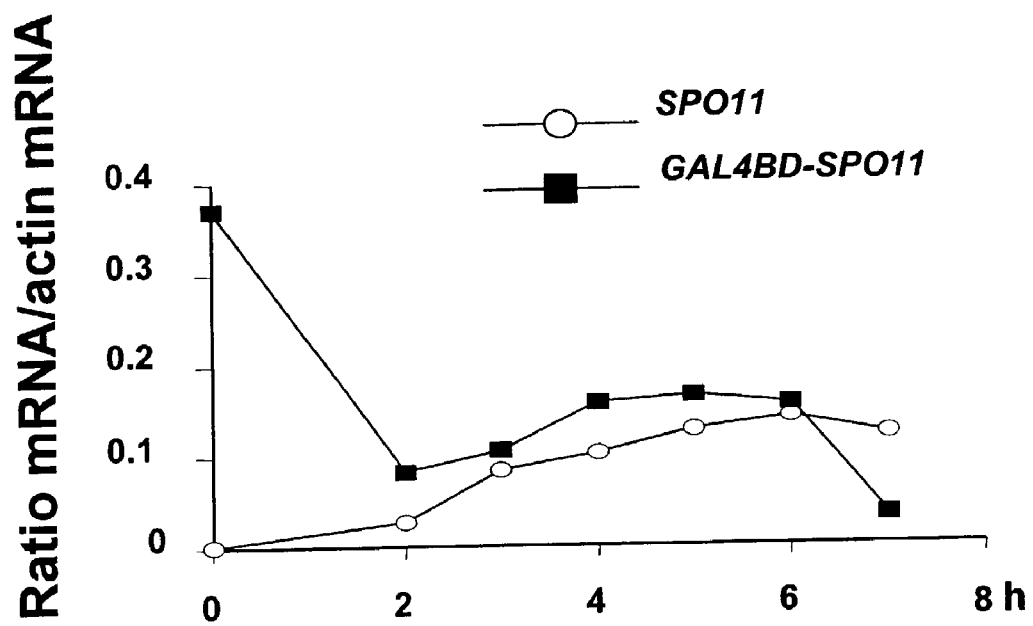
Figure 1D:
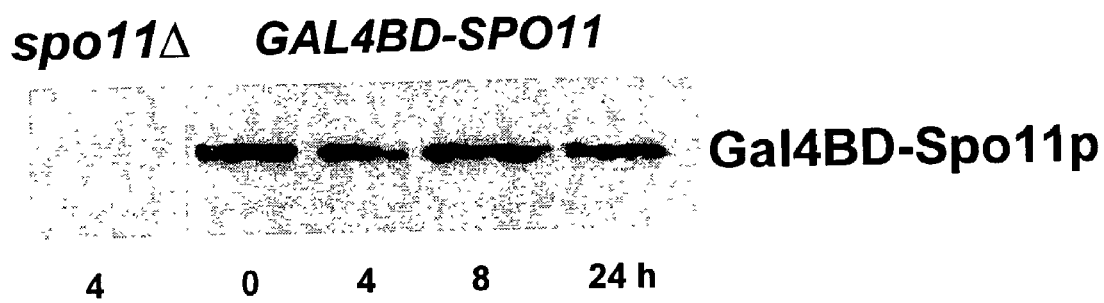

To verify expression, total RNA was analyzed during vegetative growth or at various times after transfer to sporulation medium and subjected to Northern blot analysis. In wild type diploids SPO11 mRNA begins to accumulate after transfer of cells to sporulation medium and decreases after 7 h, by which time ascospore formation has begun (FIG. 1B). In contrast, GAL4BD-SPO11 mRNA is detected in both vegetative and meiotic cells, but like SPO11 mRNA, it decreases at later timepoints (6-7 h). Quantification of transcript levels (FIG. 1C) indicates that the fusion is highly expressed in vegetatively growing cells and that the levels of GAL4BD-SPO11 mRNA are only slightly greater than the levels of SPO11 mRNA during meiotic prophase (2-6 h), most likely because the ADH1 promoter is less active in meiotic than in mitotic cells whereas the SPO11 promoter is strongly induced. Finally, western blot analysis shows that the fusion protein is expressed in both mitotic and meiotic GAL4BD-SPO11 cells and is of the expected size, 63.5 kDa (FIG. 1D).

1.2. Gal4BD-Spo11 Complements the Sporulation Defect of a spo11Δ Strain

Diploid spo11Δ cells can sporulate but produce inviable progeny because chromosomes segregate abnormally when meiotic recombination is not initiated. The inventors examined whether the Gal4BD-Spo11 protein could complement the sporulation defects of a spo11Δ diploid. Like wild type SPO11 (ORD5740) and spo11Δ (ORD5805) strains, a GAL4BD-SPO11 spo11Δ diploid (ORD5806) sporulates efficiently (approximately 80%), giving rise primarily to four-spored asci. Tetrad analysis shows that, as expected, none of the spores produced by spo11Δ diploids germinates (0/512). In contrast, the Gal4BD-Spo11 fusion protein restores full viability to spo11Δ spores (531/552, 96%), the same as observed for progeny of the SPO11 diploid (505/526, 96%). High spore viability was similarly found for a diploid that contains both GAL4BD-SPO11 and SPO11 (ORD5817). Altogether, these results demonstrate that the GAL4BD-SPO11 construct is functional and that it confers no adverse effect.

1.3. Gal4BD-Spo11 Promotes DSB Formation at Natural Sites

Figure 2A:
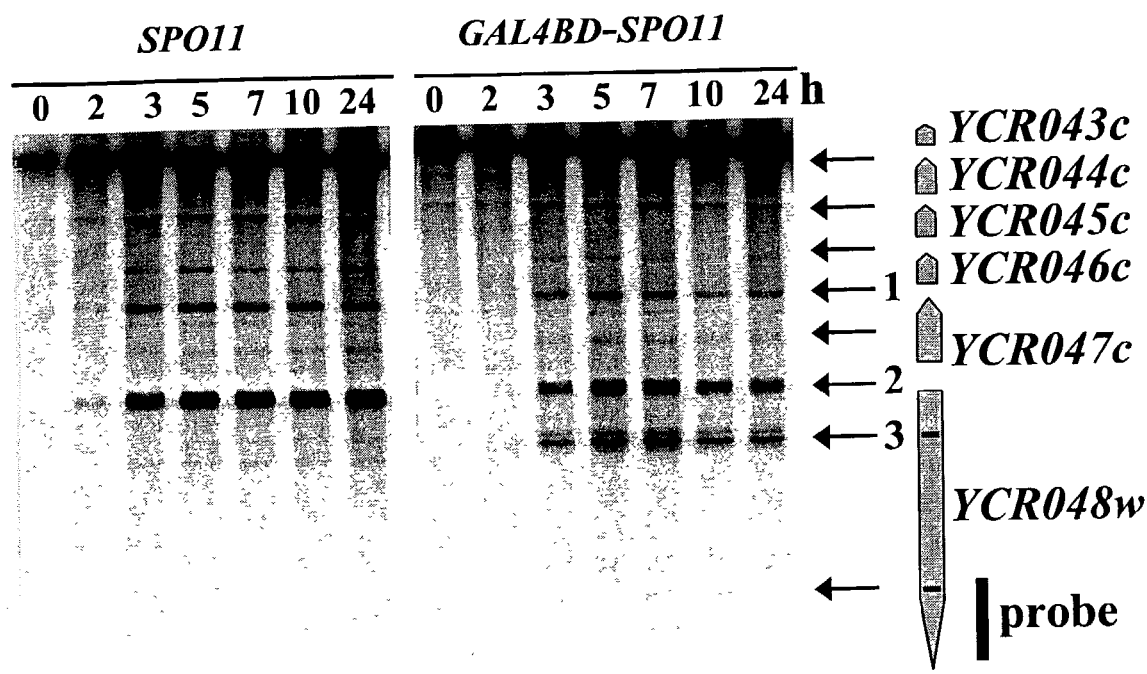
Figure 2B:
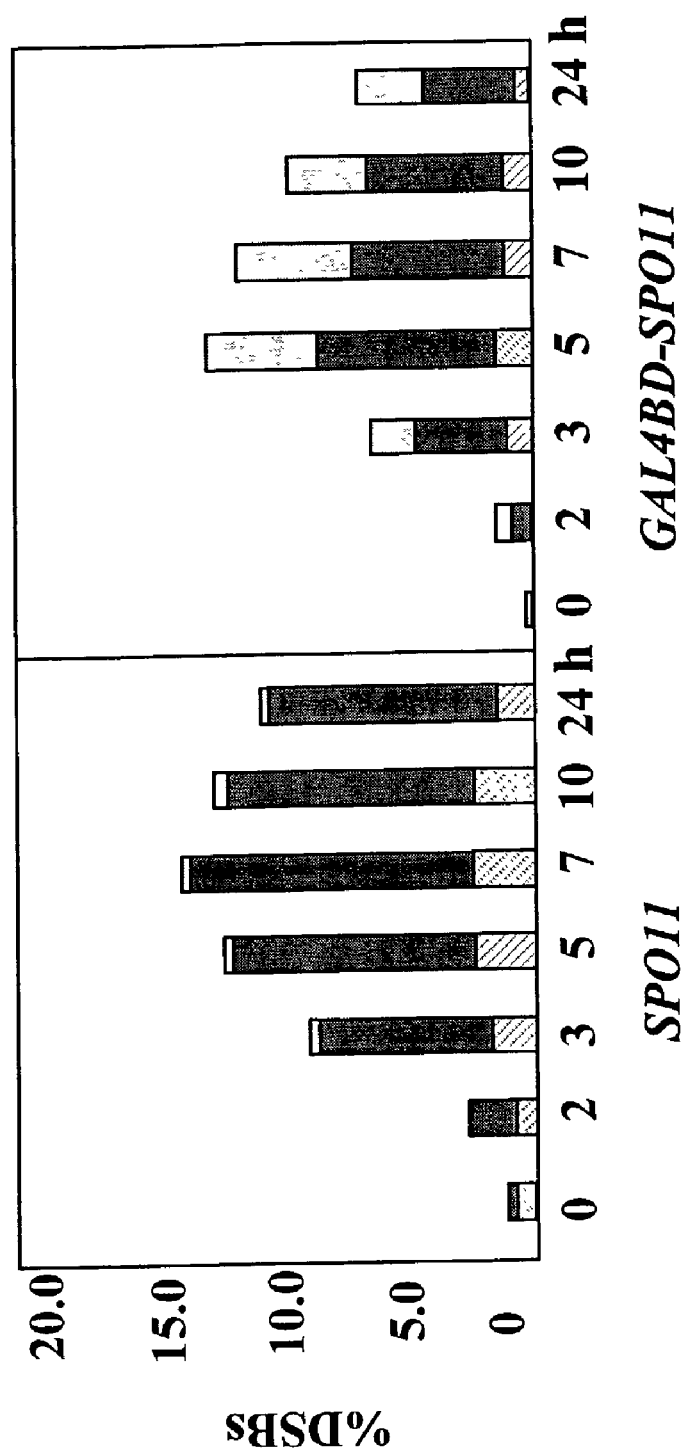
Figure 2C:
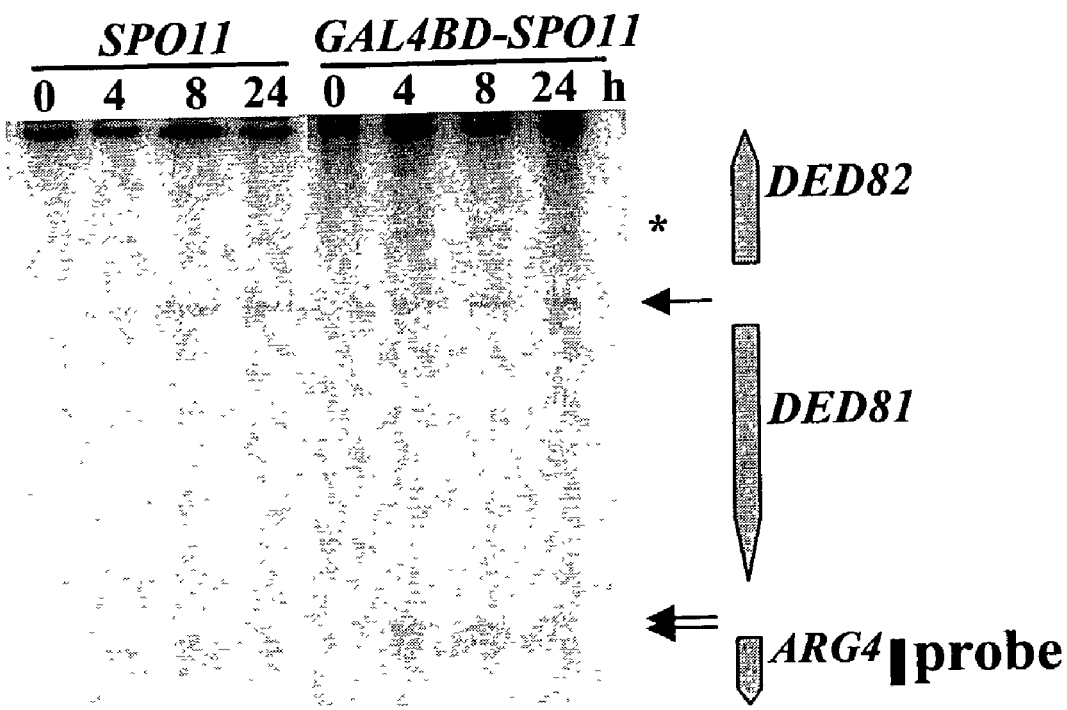
Figure 2D:
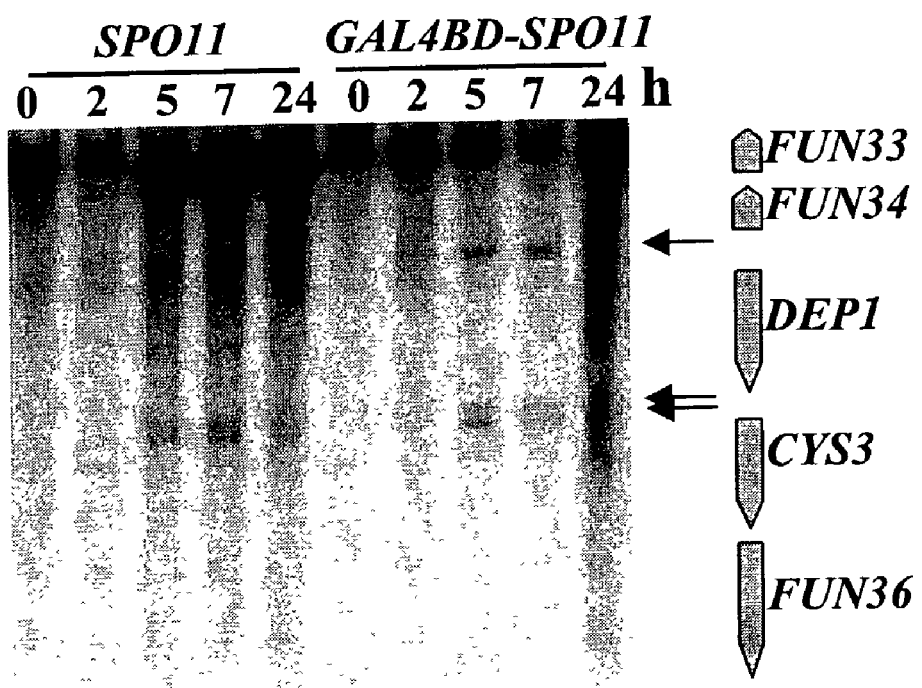

Since spore viability depends on meiotic recombination between each of a pair of homologous chromosomes, the complementation of the spo11Δ defect by GAL4BD-SPO11 suggested that the fusion protein might also rescue the spo11Δ DSB defect. To test this idea, several regions of the genome at which meiotic DSBs normally form were examined. The YCR043c-YCR048w region of chromosome III contains numerous DSB sites, including a strong hotspot in the YCR047c-048w intergenic region (Baudat and Nicolas, 1997). As shown in FIG. 2A, these DSBs are formed in both SPO11 and GAL4BD-SPO11 meiotic cells. In the GAL4BD-SPO11 strain two new DSB sites can be seen within the YCR048w coding region, which is notable since natural DSBs are generally restricted to promoter-containing regions (FIG. 2A, and see below). A quantitative analysis of DSB band intensity indicates that the cumulative frequency of meiotic DSBs in this 9.6 kb chromosomal region is similar in both strains (approximately 13±2%). In most cases, the DSB frequency at a given site is also similar, although DSBs form at a lower frequency in the YCR047c/48w intergenic region in the GAL4BD-SPO11 diploid than in the SPO11 diploid (5±1% versus 11±1%, respectively) (FIG. 2B). Interestingly, the decrease in DSB frequency at this site is locally offset by the appearance of new DSBs in the YCR048w ORF (4±1%); this redistribution is suggestive of competition between adjacent DSB sites, as previously reported for Spo11-initiated DSBs (Wu and Lichten, 1995). Two other well characterized regions were also examined, the ARG4 (on chromosome VIII) and CYS3 (on chromosome 1) loci (Vedel and Nicolas, 1999). In both cases, similar meiotic DSB profiles in SPO11 and GAL4BD-SPO11 cells were detected, with respect to positioning and intensity (FIGS. 2C and 2D). Altogether, these results demonstrate that the Gal4BD-Spo11 protein can promote DSB formation at natural sites at frequencies comparable to those promoted by wild type Spo11, thereby explaining its ability to fully complement the inviability of spo11Δ spores.

1.4. Gal4BD-Spo11 Promotes DSB Formation Near Consensus Gal4 DNA Binding Sites As described above, two additional DSB sites in the YCR048w coding region were observed: a strong site near the 5' end of the YCR048w ORF and a much weaker site further downstream (FIG. 2A). These new sites could result from an aberration in the targeting specificity of the Spo11 protein domain per se, at least in regions such as the YCR048w locus where Spo11 is already active, or they might reflect the fortuitous presence of Gal4 consensus binding sites. Indeed, an examination of the YCR048w sequence reveals two such sites within the ORF, at positions +295 and +1320 nt from the translational start site, respectively, which correlate with the estimated locations of the two new Gal4BD-Spo11-specific DSBs at this locus. This observation indicates that the Gal4BD-Spo11 protein can target DSBs to specific sequences, at least in this DSB proficient domain (Baudat and Nicolas, 1997).

Figure 3A:
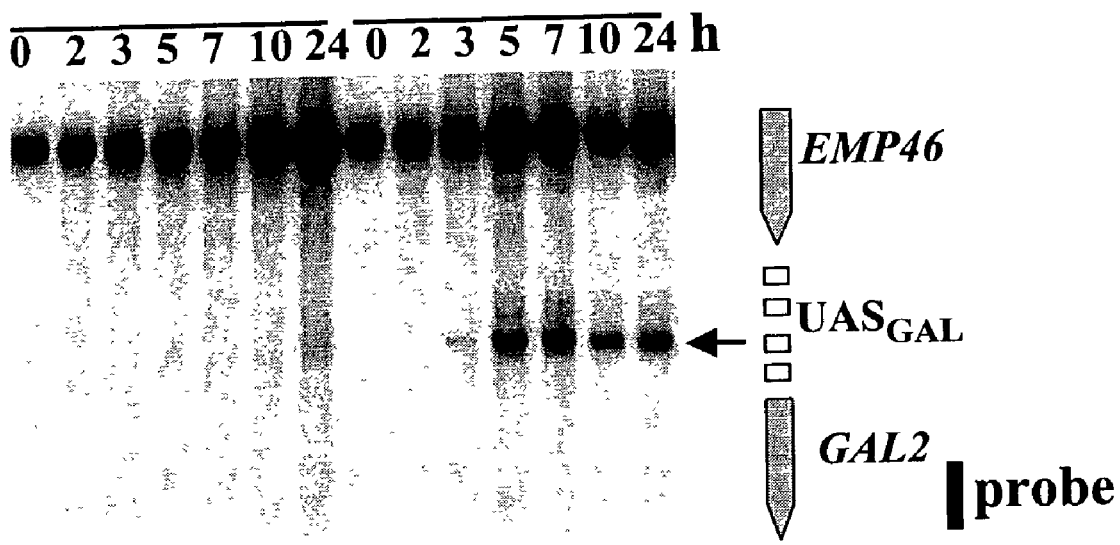

To determine whether the tethering of the Gal4 DNA binding domain to Spo11 allows meiotic DSBs to be targeted to well-characterized Gal4 binding sites, the inventors examined several loci containing $UAS_{GAL}$ sites that have been implicated in galactose catabolism. The GAL2 promoter region contains four $CCG(N)_{11}GGC$ sequences (verified by sequencing the GAL2 promoter of ORD6632), two of which are constitutively bound by Gal4 in vivo (Huibregtse et al.; 1993). In a SPO11 strain, DSBs are barely detectable at the GAL2 locus, indicating that this region is not a frequent natural DSB site. In contrast, in a GAL4BD-SPO11 strain, prominent DSBs can be observed in the GAL2 promoter near or at the $UAS_{GAL}$ sites (FIG. 3A). Similar to what was observed for the YCR043c-YCR048w interval, DSBs appear at the GAL2 locus in GAL4BD-SPO11 meiotic cells within 2 hrs of transfer of cells to sporulation medium, and their intensity increases over the course of meiosis, reaching a maximum at 8-10 h (FIG. 3A). Quantitative analysis of several independent experiments indicates that the frequency of GAL2 DSBs in the GAL4BD-SPO11 strain is approximately 12±2%, in contrast to ≦0.6% observed in the wild type strain, a 20-fold stimulation (FIG. 3).

Figure 3B:
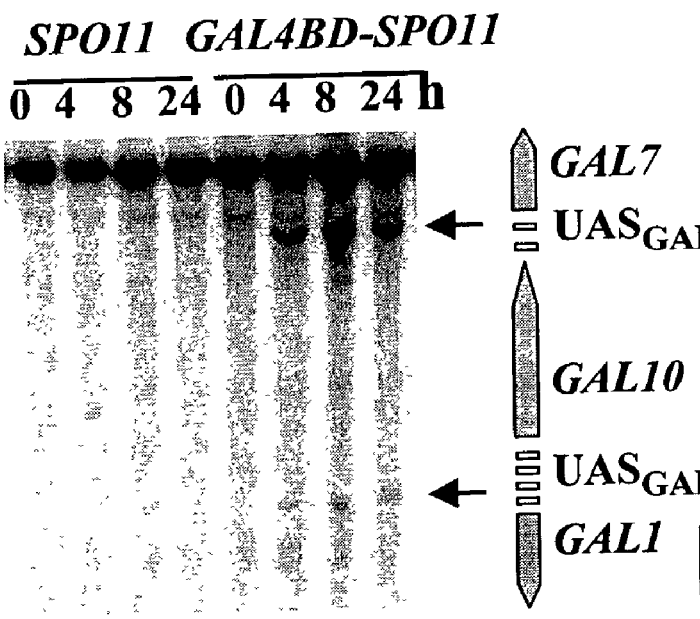

To generalize these observations, the inventors examined DSB targeting near the GAL7, GAL10 and GAL1 genes, which like GAL2 are transcriptionally induced by the Gal4 protein in the presence of galactose. At these loci, meiotic DSBs do not form in SPO11 diploids but in contrast are readily detectable at or near their associated $UAS_{GAL}$ sites in GAL4BD-SPO11 diploids (FIG. 3B). Quantitative analysis indicates a substantial stimulation of DSB formation, with frequencies of 4±1% for the GAL7 upstream region and 2±1% for the divergently transcribed GAL1-GAL10 intergenic region. This is notably lower than the frequency of 12±2% observed for the GAL2 promoter (FIG. 3A). Altogether, these results show that the Gal4BD-Spo11 protein can target meiosis-specific DSBs to Gal4 DNA binding sites, creating novel genomic DSB sites of various strenght.

Finally, it was verified with several control strains that the Gal4BD-Spo11 fusion protein is solely responsible for the appearance of these new DSBs. First, spo11Δ strains expressing the Gal4BD-spo11Y135F fusion protein, in which the Spo11 catalytic tyrosine residue is replaced with a catalytically inert phenylalanine residue (Bergerat et al., 1997), do not exhibit meiotic DSBs either in the YCR043c-YCR048w region or at the GAL2 focus. Second, SPO11 strains expressing the Gal4 binding domain either alone or fused to the Rpb5 protein (an RNA polymerase subunit whose function is unrelated to the initiation of recombination), and a strain expressing a pADH1::SPO11 construct (without Gal4BD) exhibit DSBs in the YCR043c-YCR048w region but not at the GAL2 locus. Collectively, these control experiments demonstrate that the stimulation of Gal4BD-Spo11-dependent DSBs near Gal4 binding sites requires both the Gal4BD and Spo11 components of the chimeric protein.

1.5. The Gal4BD-Spo11 Fusion Strongly Stimulates Recombination at the GAL2 Locus The above DSB experiments were performed in rad50S strains, from which viable recombinants cannot be recovered. To determine whether the new GAL4BD-SPO11-promoted DSBs are recombinogenic, meiotic DSB fragments in the GAL2 region in a RAD50 background were first examined to see if they are processed like Spo11-induced DSBs. DSBs were detected (FIG. 4A) as a smear of fragments of greater mobility than the discrete rad50S band, showing that the new GAL2 DSBs undergo processing. Moreover, the transient nature of the smear (appearing by 3 h and disappearing between 7-9 h) suggests that these DSBs are repaired with normal kinetics.

To assess whether Gal4BD-Spo11-dependent DSBs are repaired by homologous recombination, the frequency of meiotic gene conversion at the GAL2 locus was then measured. For this purpose, a mutant allele, gal2-Bsp, was constructed. This mutant allele contains a frame-shift at position 197 of the GAL2 ORF and derived GAL2/gal2-Bsp heterozygotes in both the SPO11 and GAL4BD-SPO11 backgrounds. From 218 four-spore tetrads produced by the SPO11 diploid, only five conversion events were found. In contrast, for the GAL4BD-SPO11 strain, 55 conversion events were observed in both directions (3:1 and 1:3) among 212 tetrads analyzed (26%), a 10-fold increase over the level observed for the SPO11 strain (FIG. 4C). Gal4BD-Spo11-promoted DSBs can also initiate recombination at other loci:tetrad analysis confirmed that the levels of meiotic gene conversion at the ARG4 natural hotspot are similar in SPO11 and GAL4BD-SPO11 diploids. These results show that the DSBs formed in the GAL2 promoter in GAL4BD-SPO11 strains are recombinogenic and behave like Spo11-induced breaks.

1.6. Gal4BD-Spo11 Promotes Cleavage Within a Large Region that is Normally Cold for DSB Formation The analysis of Gal4BD-Spo11 activity to a large interval of approximately 20 kb centered on GAL2 (between the YLR072w and YLR084c ORFs on chromosome XII) that contains eight intergenic promoter-containing regions (FIG. 5A). In a SPO11 strain, no DSBs were observed in this interval. In a GAL4BD-SPO11 strain, the GAL2 promoter region is the only site at which a DSB can be detected. Since there are no other Gal4 consensus sequences in this interval, these results underscore three important features of Gal4BD-Spo11 DSB activity. First, the stimulation of DSBs near GAL2 is specifically targeted. Second, cleavage at GAL2 does not promote the nearby formation of other DSBs. Third, in contrast to what is observed for DSBs in the YCR048w region of chromosome III, the new GAL2 DSBs occur in a naturally cold chromosomal region.

1.7. DSB Formation by Gal4BD-Spo11 Requires the Activity of the Other Known DSB Genes In addition to SPO11, 14 other genes are known to be required for the formation of wild type levels of DSBs at natural sites in *S. cerevisiae*. If one or more of their products is necessary to recruit Spo11 to future DSB sites, the addition of the Gal4 DNA binding domain to Spo11 might bypass this requirement, at least for DSBs at Gal4 binding sites. Southern blot analysis indicates that rec102, rec103/ski8, rec104, rec114, mei4, mer2/rec107, mre2/nam8, mre11, rad50 and xrs2 null mutants, in either the SPO11 or GAL4BD-SPO11 background, do not exhibit meiotic DSBs in the YCR043c-YCR048w interval or at GAL2 (FIG. 6), whereas the red1 mre4/mek1, hop1 and mer1, null mutants exhibit reduced but still detectable levels of DSBs. Quantitatively, at the GAL2 locus, the red1 mutation reduces the frequency of Gal4BD-Spo11 promoted DSBs by about 3-fold, the mre4/mek1 and hop1 mutations confer a 10-fold reduction, and the mer1 mutation almost completely eliminates DSB formation. Somewhat differently, in the YCR047c-48w region (YCR048w promoter+ORF), the mre4/mek1 mutation has no effect in either SPO11 or GAL4BD-SPO11 strains, and the red1, mer1 and hop1 mutations have increasingly repressive effects in both strains. The differential effects of each of these mutations on chromosome III and at GAL2 may reflect locus-specific variation. Overall, since all of these genes, which are either essential or important for DSB formation in SPO11 strains are similarly required in GAL4BD-SPO11 strains, it can be concluded that they do not assist Spo11 in target site selection.

1.8. Gal4BD-Spo11 Cleavage also Requires Clb5 Clb6 Activity

The B-type cyclins CLB5 and CLB6 are required for meiotic replication and for meiotic DSB formation. To determine whether Gal4BD-Spo11-promoted DSBs also depend on Clb5 and Clb6 activity, DSB formation was assayed in clb5 and clb5 clb6 diploids containing the GAL4BD-SPO11 construct (ORD6534 and ORD6551, respectively). As indicated in FIG. 6, no DSB formation was detected at either the YCR048w or the GAL2 locus in these strains, demonstrating that the addition of a heterologous DNA binding domain to Spo11 does not bypass the requirements for Clb5 and Clb6 activity and hence does not overcome the meiotic replication defect that is relevant to DSB induction. In conjunction with the demonstrated requirement for the other DSB genes, this result indicates that the Gal4DB-Spo11 protein is subject to the same (trans-acting) genetic controls as the Spo11 protein for DSB formation in both natural and targeted domains.

Example 2

Targeted Stimulation of Meiotic Recombination in Plants

The cDNA encoding the AtSPO11-1 protein (Grelon, Vezon et al 2001) has been amplified by PCR using the 2 oligonucleotides MG133 5'GAAACTCGGGATCCATG-GAGGGAAAAATTC3' (SEQ ID NO:1 and MG1345' GGAGACTCGCTCGAGGCTCAAGGAGA 3' (SEQ ID NO:2), cloned in pCR-BluntII-Topo (In Vitrogen) and sequenced, leading to the plasmid pVeCM2. From pVeCM2, the cDNA has been recloned between the BamH1 and Spe1 sites of pBluescript KS leading to the plasmid pVeCM12. The DNA fragment coding the Gal4 DNA binding domain (GAL4BD) has been amplified by PCR from the pAPl plasmid using the two oligonucleotides CM1 5' gaCTGCA-gaaagagATGAAGCTACTGTCTTCTAT 3' (SEQ ID NO:3) and CM2 5' CGGGGCCTCCATGGCCATAAA 3' (SEQ ID NO:4). This PCR fragment, corresponding to the ATG-Nco1 fragment of GAL4BD (455 bp), has been cloned in pCR-BluntII-Topo leading to the plasmid pVeCM15 and sequenced. The Pst1-Nco1 DNA fragment from pVeCM15 containing Gal4BD and in 5' of its ATG 8 bases corresponding to the −8 to −1 bases upstream the AtSPO11-1 ATG and the Pst1 site (CTGCAgaaagagATG) (SEQ ID NO:5), has been cloned in pVeCM12 between Pst1 and Nco1 sites, leading to the plasmid pVeCM20. pVeCM20 contains a Pst1 site followed by −8 to −1 bases of AtSPO11-1, the GAL4BD followed in fusion by the complete cDNA of AtSPO11-1 (1089 bp). A fragment of the AtSPO11-1 promoter (Gene bank AP000375) isolated by Mathilde Grelon has been amplified by PCR using the 2 oligonucleotides CM3 5' ccatctcttcTGCAGtcaaaactgaaaaatg 3' (SEQ ID NO:6) and CM4 5' ATGGGCCCgcctttgttttatctctcctcaccgta 3' (SEQ ID NO:7), cloned in pCR-BluntII-Topo, leading to the plasmid pVeCM14, and sequenced. The Apa1-Pst1 fragment from pVeCM14 containing the −1352 to −8 bases of the AtSPO11-1 promoter has been cloned in pVeCM20 between Apa1 and Pst1, leading to the plasmid pVeCM22. Then the Apa1-BseR1 fragment containing the −2266 to −1324 region of AtSPO11-1 has been cloned in pVeCM20 between the Apa1 and BseR1 sites leading to the plasmid pVeCM25. The Apa1-Spe1 fragment from pVeCM25 containing the construct AtSPO11-1 promoter/GAL4BD-AtSPO11-1 cDNA has been resequenced. An insertion of 11 nucleotides (CCCATCTCTTT) (SEQ ID NO:8) was present just in 5' of the Pst1 cloning site. The promoter hence corresponds to the −2266 to −1 bases of the At promoter, with an insertion of 11 nucleotides just in 5' of the Pst1.

The stimulation of meiotic recombination is then determined by analysis of microsatellite markers that exist upstream and downstream of the natural targets for GAL4BD that exist in the Arabidopsis genome (more than 40 with the more stringent consensus sequence, and up to several hundreds with the most degenerated, i.e., only the 3 bp on each side of the UAS), in homozygous mutants and wild-type strains.

A cell line exhibiting two resistance gene as markers, separated by one GAL4BD recognition sequence, is also constructed, in order to study the crossing-over between these two markers.

Example 3

Induction of Site-Directed and/or Increased Meiotic Recombination in Mice

The Sycp1 gene, coding for the murine synaptonemal complex, is expressed in both zygotene and pachytene phases of the meiosis (Sage, Martin et al. 1999). Therefore, it can be used to express a spo11 gene in meiosis early stages. The expression of the Gal4BD-mSpo11 fusion protein in early stage of meiosis has three advantages: it enables the targeting of meiotic recombination at new sites and help to follow-up the impact of initiating recombination on associated chromosome changes and on the mouse development.

The Gal4BD-mSPO11 chimerical DNA is placed under the control of the region upstream the Sycp1 coding sequence or another promoter fragment functional in early meiosis, in a bacterial plasmid.

A sequence coding for a Gal4BD-mSPO11 fusion protein, wherein mSPO11 protein is the murine Spo11 protein, is constructed by placing the Gal4BD coding sequence in phase with the murine spoil sequence described by Metzler-Guillemain C. and B. de Massy (2000). This can be done for example by using the following multistep cloning strategy the Gal4BD fragment of pAPl is amplified by PCR using primers APG4up (5'GAGATTAATTAAGGCCATAT-GAAGCTACTGTCTTCTATCGAA) (SEQ ID NO:9) and APG4LO (5'AATCCTGTTAACAATGCTTTT) (SEQ ID NO:10), and cloned into the pGEM-T Easy (Promega) and sequenced, creating pAP15 containing a NdeI site overlapping the ATG translation start site of the Gal4BD sequence.

Next, pAP15 is cleaved by PacI-HpaI and the fragment containing the 5' Gal4BD (NdeI containing site) sequence is cloned into the pAP1 vector, cleaved by PacI-HpaI to remove the pADH1 promoter, creating the plasmid pAP16.

Next, pA16 is cleaved by PacI-SacI to remove the KanMX marker (G418 resistance), blunted and religated to create pAP17.

The BamHI-PstI fragment of pAP17 containing the *S. cerevisiae* Spo11 fragment is then substituted by the BglII-PstI fragment of pCMVβ (Clontech) containing a SV40 polyadenylation site to create plasmid pAP3.

Next, the EcoRI-SalI blunted-filled fragment of pTAg 0.8 containing the promoter of SyCP1, is blunted-filled and cloned into the EcoRI site of pAP3, creating pAP18.

The EcoRI fragment of plasmid pGEM-tSPO11s, containing the mouse SPO11 cDNA, is then amplified by PCR with primers to add flanking SfiI and XmaI restriction sites and cloned into the pGEM-t Easy vector (Promega), creating plasmid pAP19 and sequenced.

Finally, the SfiI-XmaI fragment of pAP19, containing the pSycp1 promoter (TaqI-EcoRI fragment) followed by the Gal4BD fragment (EcoRI-SfiI), is fused to the mouse SPO11 cDNA (SfiI-XmaI fragment) and terminated by the polyA fragment (XmaI-PstI), creating a modular cassette for convenient exchange of the various components, carried by a vector allowing multiplication in bacteria.

This pGal4BD-mSpo11 plasmid is linearized and introduced by micro-injection in a mouse egg. Mice are then selected by genomic DNA analysis with a probe specific for the Sycp1/Gal4BD-mSpo11 transgene. Independent Sycp1/Gal4BD-mSpo11 transgenic families are then established though cross breedings with normal and characterized mice.

The meiotic functionality of the transgene expresion is then determined in the wild-type and mutant mice inactivated for the mSPO11 gene (Baudat, Manova et al. 2000) by observation of the effect on the fertility of the animals and monitoring meiotic recombination frequencies between polymorphic markers in the progeny, the gametes or in a preparation of meiotic cells by Southern blot or PCR techniques, probing a chromosomal region containing a consensus recognition site for the Gal4 protein. This target site is either a natural or transgenic sequence carrying one or more copies of the GAL4 UAS motif.

Example 4

Improvement of Homologous Recombination in Drosophila

Drosophila offers many advantages as an experimental organism. However, in comparison with yeast and mouse, two other widely used eukaryotic model systems, Drosophila suffers from an inability to perform homologous recombination between introduced DNA and the corresponding chromosomal loci. The ability to specifically modify the genomes of yeast and mouse provides a quick an easy way to generate or rescue mutations in genes for which a DNA clone or sequence is available. Recently, Rong and Golic have developed a new technique for targeted homologous recombination, using the intron restriction enzyme I-SceI as an inductor of double strand break in linear molecules of DNA generated from flip recombinase excision of DNA (Rong and Golic 2000). In this way, they rescued yellow mutation (Rong and Golic 2000) and disrupted the pugilist gene and, more recently, the NlacZ, GC, p53 and CG11305 genes. This knock out technique has very low efficiency, and the mutation is generated in two steps.

The Gal4BD-Spo11 fusion protein, described in Example 1, can be used instead of I-SceI enzyme in order to develop a new approach to generate "knock outs" in Drosophila, and to improve the efficiency of the targeted homologous recombination. To this aim, the sequence coding for Gal4BD-Spo11 has been inserted in an expression vector for the Drosophila (P(Casper-hs), Pirrotta 1988). In this vector, the Gal4BD-Spo11 sequence is placed under the control of a heat shock promoter. Five different insertions of this transposable have been obtained in Drosophila.

The rescue of meiW68 sterility phenotype (McKim and Hayashi-Hagihara 1998) in Spo11 homologous Drosophila is tested, with the induction of Gal4-Spo11 during the developmental time where the gametes are generated.

The I-SceI recognition sequence over the yellow gene is replaced by UAS sequences, recognized by the GAL4 binding domain (using P elements), and gal4-meiW68 strains are constructed. The Rong and Golic yellow rescue is repeated to compare efficiencies of the two methods.

To perform these experiments, the following plasmids are used:
Expression vector: pCasper-hs (Pirrotta 1988)
Heat shock promoter hsP70 (Pirrotta 1988)
Targeted p(UAS): y-donor (Rong and Golic 2000) modified by replacement of 1-Scel site by UAS sequences (five)

The Drosophila strain used in these experiments is Canton-Special (CS) $y^1$.

As described above, the methods to assay the effect of Gal4-Spo11 are the rescue of mei-W68 phenotype and the rescue of $y^1$ (normal body color).

Example 5

Stimulation of Meiotic Recombination Between Poorly Recombining Chromosomes

Efficient genetic recombination between homologous chromosomes requires the formation of an initiating lesion such as a DNA double-strand break formed by the Spo11 protein as exemplified in Example 1. Thus, chromosomes devoid of Spo11 target sites will poorly recombine. The Gal4Bd-Spo11 fusion protein, described in Example 1, can be used to stimulate the initiation of recombination at natural or artificially introduced Gal4 binding sites along any natural or artificial (YACs) chromosomes consisting of yeast or non-yeast DNA. Similarly, recombination might be stimulated between yeast linear plasmids with bacteriophage λ DNA backbones that poorly recombine.

Efficient genetic recombination also requires near-perfect homology between the participating molecules. According to their degree of divergence, homeologous chromosomes variably recombine in meiosis and as a consequence of the reduced level of crossing-over, gametes viability decreases and the proportion of aneuploid products increase consistently with defects in meiosis I or II non-disjunction of the homeologs. Homeologous chromosomes V of Saccharomyces cerevisiae and Saccharomyces carlbergensis virtually do not recombine in meiosis, but artificially created short regions of homology were found to induce meiotic crossing-over, probably by facilitation of heteroduplex intermediate formation initiated at adjacent sites. The Gal4BD-Spo11 fusion protein, described in Example 1, can be used to stimulate the initiation of recombination at natural or artificially introduced Gal4 binding sites along any natural or artificial (YACs) chromosomes consisting of yeast or non-yeast homeologous DNA.

Example 6

Stimulation of Homologous Recombination in Mitotic Cells

High level of homologous recombination during meiosis is induced by the formation of Spo11-High level of homologous recombination during meiosis by the formation of Spo11-dependent Double-strand breaks, that also require the expression of at least 14 other proteins (called DSB genes in Example 1). Some of them are only expressed upon the induction of meiosis. Taking advantage of the novel DNA binding property of the Gal4BD-SPO11 fusion protein, that allow to bypass the requirement for the trans-acting factor that brings Spo11 to its target sites, the attempt to obtain Spo11-dependent DNA cleavage activity in mitotic cells is achieved by expressing the additional genes required for DSB formation in mitotic cells. This can be achieved by several approaches: heterologous expression of the individual genes and/or of cDNA genomic library behind a mitotically expressed promoter, or by a mutational change of the transcription factor(s) that repress their expression in mitotically growing cells.

REFERENCES

Alani, E., Padmore, R., and Kleckner, N. (1990). Analysis of wild-type and rad50 mutants of yeast suggests an intimate relationship between meiotic chromosome synapsis and recombination. Cell 61, 419-436.

Ausubel, F. M., Brent, R., Kingston, R. E., Moore, D. D., Seidman, J. G., Smith, J. A., and Strul, K. eds. (1988). Current Protocols in Molecular Biology. (New York: John Wiley & Sons, Inc.).

Baudat, F., and Nicolas, A. (1997). Clustering of meiotic double-strand breaks on yeast chromosome III. Proc. Natl. Acad. Sci. USA 94, 5213-5218.

Baudat, F. Madova, K., Yuen, J. P., Jasin, M., and Keency, S. (2000) Chromosome synapsis defects and sexually dimorphic meiotic progression in mice lackin Spo11. Molecular Cell, 6: 989-998.

Bergerat, A., de Massy, B., Gadelle, D., Varoutas, P. C., Nicolas, A., and Forterre, P. (1997). An a typical topoisomerase II from Archaea with implications for meiotic recombination. Nature 386, 414-417.

Beretta, G. L., Binaschi, M., Zagni, E., Capuani, L., and Capranico, G. (1999). Tethering a type IB topoisomerase to a DNA site by enzyme fusion to a heterologous site-selective DNA-binding protein domain. Cancer Res. 59, 3689-3697.

Borde, V., Wu, T. C., and Lichten, M. (1999). Use of a recombination reporter insert to define meiotic recombination domains on chromosome III of *Saccharomyces cerevisiae*. Mol. Cell. Biol. 19, 4832-4842.

Diaz, R. L., Alcid, A. D., Berger, J. M., and Keeney, S. (2002). Identification of residues in yeast Spo11p critical for meiotic DNA double-strand break formation. Mol. Cell. Biol. 22, 1106-1115.

Esposito, M. S. and Esposito, R. E. (1969). "The genetic control of sporulation in *saccharomyces*. I. The isolation of temperature-sensitive sprorulation-deficient mutants"—Genetics, 61:79-89.

Fromont-Racine, M., J. C. Rain, et al. (1997). "Toward a functional analysis of the yeast genome through exhaustive two-hybrid screens." Nat Genet 16(3): 277-82.

Gerton, J. L., DeRisi, J., Shroff, R., Lichten, M., Brown, P. O., and Petes, T. D. (2000). Global mapping of meiotic recombination hotspots and coldspots in the yeast *Saccharomyces cerevisiae*. Proc. Natl. Acad. Sci. USA 97, 11383-11390.

Grelon, M., D. Vezon, et al. (2001). "AtSPO11-1 is necessary for efficient meiotic recombination in plants." Embo J 20(3): 589-600.

Kane, S. M., and Roth, R. (1974). Carbohydrate metabolism during ascospore development in yeast. J. Bacteriol. 118, 8-14.

Huibregtse, J. M., Good, P. D., Marczynski, G. T., Jaehning, J. A., and Engelke, D. R. (1993). Gal4 protein binding is required but not sufficient for depression andinduction of GAL2 expression. J. Biol. Chem. 268:22219-22222.

Keeney, S., Giroux, C. N., and Kleckner, N. (1997). Meiosis-specific DNA double-strand breaks are catalyzed by Spo11, a member of a widely conserved protein family. Cell 88, 375-384.

Keeney, S. (2001). The mechanism and control of meiotic recombination initiation. Curr. Top. Dev. Biol. 52, 1-53.

Metzler-Guillemain, C. and B. de Massy (2000). "Identification and characterization of an SPO11 homolog in the mouse." Chromosoma 109(1-2): 133-8.

McKim, K. S. and A. Hayashi-Hagihara (1998). "mei-W68 in *Drosophila melanogaster* encodes a Spo11 homolog: evidence that the mechanism for initiating meiotic recombination is conserved." Genes Dev 12(18): 2932-42.

Ohta, K., Shibata, T., and Nicolas, A. (1994). Changes in chromatin structure at recombination initiation sites during yeast meiosis. EMBO J. 13, 5754-5763.

Petes, T. D. (2001). Meiotic recombination hot spots and cold spots. Nature Reviews 2, 360-369.

Pirrotta, V. (1988). "Vectors for P-mediated transformation in *Drosophila*." Biotechnology 10: 437-56.

Ren, B., Robert, F., Wyrick, J., Aparicio, O., Jennings, E., Simon, I., Zeitlinger, J., Schreiber, J., Hannett, N., Kanin, E., Volkert, T. L., Wilson, C. J., Bell, S. P. and Young, R. A. (2000). Genome-wide location and function of DNA binding proteins. Science 290, 2306-2309.

Rong, Y. S. and K. G. Golic (2000). "Gene targeting by homologous recombination in *Drosophila*." Science 288 (5473): 2013-8.

Sage, J., L. Martin, et al. (1999). "Temporal and spatial control of the Sycp1 gene transcription in the mouse meiosis: regulatory elements active in the male are not sufficient for expression in the female gonad." Mech Dev 80(1): 29-39.

Sherman, A., Fink, G. R., and Hicks, J. (1983). Methods in Yeast Genetics (Cold Spring Harbor, N.Y., Cold Spring Harbor Laboratory Press).

Sikorski, R. S., and Hieter, P. (1989). A system of shuttle vectors and yeast host strains designed for efficient manipulation of DNA in *Saccharomyces cerevisiae*. Genetics 122, 19-27.

Smith, K. N., Penkner, A., Ohta, K., Klein, F., and Nicolas, A. (2001). B-type cyclins CLB5 and CLB6 control the initiation of recombination and synaptonemal complex formation in yeast meiosis. Curr. Biol. 11, 88-97.

Vedel, M., and Nicolas, A. (1999). CYS3, a hotspot of meiotic recombination in *Saccharomyces cerevisiae*: effects of heterozygosity and mismatch repair functions on gene conversion and recombination intermediates. Genetics 151, 1245-1259.

Wach, A. (1996). PCR-synthesis of marker cassettes with long flanking homology regions for gene disruptions in *Saccharomyces cerevisiae*. Yeast 12, 259-265.

Wu, T.-C., and Lichten, M. (1994). Meiosis-induced double-strand break sites determined by yeast chromatin structure. Science 263, 515-518.

Wu, T.-C., and Lichten, M. (1995). Factors that affect the location and frequency of meiosis-induced double-strand breaks in *Saccharomyces cerevisiae*. Genetics 140, 55-66.

What we claim is:

1. A method for performing a targeted recombination between two or more polymorphisms carried by a same chromosome in a cell, comprising the steps of:
   (i) introducing into said cell, a nucleic acid encoding a fusion protein comprising a DNA binding domain operably linked to a Spo11 protein, wherein said DNA binding domain recognizes a sequence situated between said two or more polymorphisms, and
   (ii) having the cell divide, so that recombination between said two or more polymorphisms in said cell occurs.

2. The method of claim 1, further comprising before step (ii), a step of introducing into said cell's genome, between said two or more polymorphisms, a DNA sequence recognized by said DNA binding domain operably linked to a Spo11 protein.

3. The method of claim 1, wherein the cell division performed in step (ii) is a meiosis.

4. The method of claim 1, wherein said cell is an eukaryotic cell.

5. The method of claim 4, wherein said cell is selected from the group of a fungus, a plant cell, a mammalian cell, and an insect cell.

6. The method of claim 1, wherein said cell comprises artificial chromosomes carrying one or more sequence(s) recognized by said DNA binding domain operably linked to the Spo11 protein.

7. The method of claim 1, wherein said cell is a fungus and the nucleic acid introduced in step (i) encodes a Gal4BD-Spo11 fusion protein.

8. The method of claim 6, wherein said cell is a yeast, said artificial chromosome is a YAC having one or more sites with a $CGGN_{11}CGG$ sequence (SE ID No:11), and said DNA binding domain operably linked to the Spo11 protein is a Gal4BD DNA binding domain.

9. A method for performing a targeted recombination between two or more polymorphisms carried by a same chromosome in a cell, comprising the steps of:
   (i) introducing into said cell, a nucleic acid encoding a fusion protein comprising a DNA binding domain operably linked to a Spo11 protein, wherein said DNA binding domain recognizes a sequence situated between said two or more polymorphisms, wherein said fusion protein is a Gal4BD-Spo11 fusion protein, and
   (ii) Having the cell divide, so that recombination between said two or more polymorphisms in said cell occurs.

* * * * *